US007408174B2

(12) United States Patent
From et al.

(10) Patent No.: US 7,408,174 B2
(45) Date of Patent: Aug. 5, 2008

(54) FLUID TREATMENT SYSTEM

(75) Inventors: Wes From, London (CA); Boyko Tchavdarov, Naperville, IL (US); Mike Marcu, Ancaster (CA); Richard Gratton, London (CA); David Olson, London (CA); Jim Fraser, London (CA); Dusko A. Kezele, London (CA)

(73) Assignee: Trojan Technologies Inc. (CA)

( * ) Notice: Subject to any disclaimer, the term of this patent is extended or adjusted under 35 U.S.C. 154(b) by 374 days.

(21) Appl. No.: 11/078,706

(22) Filed: Mar. 14, 2005

(65) Prior Publication Data

US 2005/0263716 A1  Dec. 1, 2005

Related U.S. Application Data

(60) Provisional application No. 60/552,185, filed on Mar. 12, 2004, provisional application No. 60/613,215, filed on Sep. 28, 2004.

(51) Int. Cl.
*B01D 17/00* (2006.01)

(52) U.S. Cl. .................. 250/436; 250/435; 250/428; 250/431; 250/438

(58) Field of Classification Search ................ 250/436, 250/435, 428, 431, 438
See application file for complete search history.

(56) References Cited

U.S. PATENT DOCUMENTS

| 4,571,392 | A | | 2/1986 | Howarth | 514/210 |
| 5,200,156 | A | * | 4/1993 | Wedekamp | 422/186.3 |
| 5,352,359 | A | * | 10/1994 | Nagai et al. | 210/192 |
| 5,418,370 | A | | 5/1995 | Maarschalkerweerd | 250/431 |
| 5,933,702 | A | * | 8/1999 | Goswami | 422/186.3 |
| 6,332,981 | B1 | * | 12/2001 | Loyd | 210/198.1 |
| 6,500,346 | B1 | * | 12/2002 | Taghipour et al. | 210/748 |
| 2005/0092932 | A1 | * | 5/2005 | Bircher et al. | 250/436 |
| 2005/0183996 | A1 | * | 8/2005 | Zemel et al. | 210/85 |

FOREIGN PATENT DOCUMENTS

| WO | WO 01/66469 | 9/2001 |
| WO | WO 2004/000735 | 12/2003 |

* cited by examiner

*Primary Examiner*—Jack I. Berman
*Assistant Examiner*—Michael J Logie
(74) *Attorney, Agent, or Firm*—Katten Muchin Rosenman LLP

(57) ABSTRACT

The present invention relates to a fluid treatment system comprising: an inlet; an outlet; and a fluid treatment zone disposed between the inlet and the outlet. The fluid treatment zone has disposed therein: (i) an elongate first radiation source assembly having a first longitudinal axis, and (ii) an elongate second radiation source assembly having a second longitudinal axis. The first longitudinal axis and the second longitudinal axis are non-parallel to each other and to a direction of fluid flow through the fluid treatment zone. The present fluid treatment system has a number of advantages including: it can treat large volumes of fluid (e.g., wastewater, drinking water or the like); it requires a relatively small "footprint"; it results in a relatively lower coefficient of drag resulting in an improved hydraulic pressure loss/gradient over the length of the fluid treatment system; and it results in relatively lower (or no) forced oscillation of the radiation sources thereby obviating or mitigating of breakage of the radiation source and/or protective sleeve (if present). Other advantages are discussed in the specification.

33 Claims, 17 Drawing Sheets

FLUID TREATMENT SYSTEM

CROSS-REFERENCE TO RELATED APPLICATION

The present application claims the benefit under 35 U.S.C. §119(e) of provisional patent application Ser. No. 60/552,185 filed on Mar. 12, 2004 and Ser. No. 60/613,215 filed on Sep. 28, 2004, the contents of each of which are hereby incorporated by reference.

BACKGROUND OF THE INVENTION

1. Field of the Invention

In one of its aspects, the present invention relates to a fluid treatment system, more particularly, an ultraviolet radiation water treatment system. In another of its aspects, the present invention relates to a method for treating a fluid, more particularly a method for irradiating water.

2. Description of the Prior Art

Fluid treatment systems are generally known in the art. More particularly, ultraviolet (UV) radiation fluid treatment systems are generally known in the art. Early treatment systems comprised a fully enclosed chamber design containing one or more radiation (preferably UV) lamps. Certain problems existed with these earlier designs. These problems were manifested particularly when applied to large open flow treatment systems which are typical of larger scale municipal waste water or potable water treatment plants. Thus, these types of reactors had associated with them the following problems:

relatively high capital cost of reactor;
difficult accessibility to submerged reactor and/or wetted equipment (lamps, sleeve cleaners, etc);
difficulties associated with removal of fouling materials from fluid treatment equipment;
relatively low fluid disinfection efficiency, and/or
full redundancy of equipment was required for maintenance of wetted components (sleeves, lamps and the like).

The shortcomings in conventional closed reactors led to the development of the so-called "open channel" reactors.

For example, U.S. Pat. Nos. 4,482,809, 4,872,980 and 5,006,244 (all in the name of Maarschalkerweerd and all assigned to the assignee of the present invention and hereinafter referred to as the Maarschalkerweerd #1 Patents) all describe gravity fed fluid treatment systems which employ ultraviolet (UV) radiation.

Such systems include an array of UV lamp modules (e.g., frames) which include several UV lamps each of which are mounted within sleeves which extend between and are supported by a pair of legs which are attached to a cross-piece. The so-supported sleeves (containing the UV lamps) are immersed into a fluid to be treated which is then irradiated as required. The amount of radiation to which the fluid is exposed is determined by the proximity of the fluid to the lamps, the output wattage of the lamps and the flow rate of the fluid past the lamps. Typically, one or more UV sensors may be employed to monitor the UV output of the lamps and the fluid level is typically controlled, to some extent, downstream of the treatment device by means of level gates or the like.

The Maarschalkerweerd #1 Patents teach fluid treatment systems which were characterized by improved ability to extract the equipment from a wetted or submerged state without the need for full equipment redundancy. These designs compartmentalized the lamp arrays into rows and/or columns and were characterized by having the top of the reactor open to provide free-surface flow of fluid in a "top open" channel.

The fluid treatment system taught in the Maarschalkerweerd #1 Patents is characterized by having a free-surface flow of fluid (typically the top fluid surface was not purposely controlled or constrained). Thus, the systems would typically follow the behavior of open channel hydraulics. Since the design of the system inherently comprised a free-surface flow of fluid, there were constraints on the maximum flow each lamp or lamp array could handle before either one or other hydraulically adjoined arrays would be adversely affected by changes in water elevation. At higher flows or significant changes in the flow, the unrestrained or free-surface flow of fluid would be allowed to change the treatment volume and cross-sectional shape of the fluid flow, thereby rendering the reactor relatively ineffective. Provided that the power to each lamp in the array was relatively low, the subsequent fluid flow per lamp would be relatively low. The concept of a fully open channel fluid treatment system would suffice in these lower lamp power and subsequently lower hydraulically loaded treatment systems. The problem here was that, with less powerful lamps, a relatively large number of lamps was required to treat the same volume of fluid flow. Thus, the inherent cost of the system would be unduly large and/or not competitive with the additional features of automatic lamp sleeve cleaning and large fluid volume treatment systems.

This led to the so-called "semi-enclosed" fluid treatment systems.

U.S. Pat. Nos. 5,418,370, 5,539,210 and Re36,896 (all in the name of Maarschalkerweerd and all assigned to the assignee of the present invention and hereinafter referred to as the Maarschalkerweerd #2 Patents) all describe an improved radiation source module for use in gravity fed fluid treatment systems which employ UV radiation. Generally, the improved radiation source module comprises a radiation source assembly (typically comprising a radiation source and a protective (e.g., quartz) sleeve) sealingly cantilevered from a support member. The support member may further comprise appropriate means to secure the radiation source module in the gravity fed fluid treatment system.

Thus, in order to address the problem of having a large number of lamps and the incremental high cost of cleaning associated with each lamp, higher output lamps were applied for UV fluid treatment. The result was that the number of lamps and subsequent length of each lamp was dramatically reduced. This led to commercial affordability of automatic lamp sleeve cleaning equipment, reduced space requirements for the treatment system and other benefits. In order to use the more powerful lamps (e.g. medium pressure UV lamps), the hydraulic loading per lamp during use of the system would be increased to an extent that the treatment volume/cross-sectional area of the fluid in the reactor would significantly change if the reactor surface was not confined on all surfaces, and hence such a system would be rendered relatively ineffective. Thus, the Maarschalkerweerd #2 Patents are characterized by having a closed surface confining the fluid being treated in the treatment area of the reactor. This closed treatment system had open ends which, in effect, were disposed in an open channel. The submerged or wetted equipment (UV lamps, cleaners and the like) could be extracted using pivoted hinges, sliders and various other devices allowing removal of equipment from the semi-enclosed reactor to the free surfaces.

The fluid treatment system described in the Maarschalkerweerd #2 Patents was typically characterized by relatively short length lamps which were cantilevered to a substantially vertical support arm (i.e., the lamps were supported at one end only). This allowed for pivoting or other extraction of the lamp from the semi-enclosed reactor. These significantly shorter and more powerful lamps inherently are characterized by being less efficient in converting electrical energy to UV energy. The cost associated with the equipment necessary to physically access and support these lamps was significant.

Historically, the fluid treatment modules and systems described in the Maarschalkerweerd #1 and #2 Patents have found widespread application in the field of municipal waste water treatment (i.e., treatment of water that is discharged to a river, pond, lake or other such receiving stream).

In the field of municipal drinking water, it is known to utilize so-called "closed" fluid treatment systems or "pressurized" fluid treatment systems.

Closed fluid treatment devices are known—see, for example, U.S. Pat. No. 5,504,335 (Maarschalkerweerd #3). Maarschalkerweerd #3 teaches a closed fluid treatment device comprising a housing for receiving a flow of fluid. The housing comprises a fluid inlet, a fluid outlet, a fluid treatment zone disposed between the fluid inlet and the fluid outlet, and at least one radiation source module disposed in the fluid treatment zone. The fluid inlet, the fluid outlet and the fluid treatment zone are in a collinear relationship with respect to one another. The at least one radiation source module comprises a radiation source sealably connected to a leg which is sealably mounted to the housing. The radiation source is disposed substantially parallel to the flow of fluid. The radiation source module is removable through an aperture provided in the housing intermediate to fluid inlet and the fluid outlet thereby obviating the need to physically remove the device for service of the radiation source.

U.S. Pat. No. 6,500,346 [Taghipour et al. (Taghipour)] also teaches a closed fluid treatment device, particularly useful for ultraviolet radiation treatment of fluids such as water. The device comprises a housing for receiving a flow of fluid. The housing has a fluid inlet, a fluid outlet, a fluid treatment zone disposed between the fluid inlet and the fluid outlet and at least one radiation source having a longitudinal axis disposed in the fluid treatment zone substantially transverse to a direction of the flow of fluid through the housing. The fluid inlet, the fluid outlet and the fluid treatment zone are arranged substantially collinearly with respect to one another. The fluid inlet has a first opening having: (i) a cross-sectional area less than a cross-sectional area of the fluid treatment zone, and (ii) a largest diameter substantially parallel to the longitudinal axis of the at least one radiation source assembly.

Practical implementation of known fluid treatment systems of the type described above have been such that the longitudinal axis of the radiation source is: (i) parallel to the direction of fluid flow through the fluid treatment system, or (ii) orthogonal to the direction of fluid flow through the fluid treatment system. Further, in arrangement (ii), it has been common to place the lamps in an array such that, from an upstream end to a downstream end of the fluid treatment system, a downstream radiation source is placed directly behind an upstream radiation source.

The use of arrangement (ii) in an UV radiation water treatment system has been based on the theory that radiation was effective up to a prescribed distance from the radiation source, depending on the transmittance of the water being treated. Thus, it has become commonplace to interspace the radiation sources in arrangement (ii) such that the longitudinal axes of adjacent radiation sources are spaced at a distance equal to approximately twice the prescribed distance mentioned in the previous sentence.

Unfortunately, for the treatment of large volumes of fluid, arrangement (ii) can be disadvantageous for a number of reasons. Specifically, implementation of arrangement (ii) requires a relatively large "footprint" or space to house the radiation sources. Further, the use of a large number of radiation sources in arrangement (ii) creates a relatively large coefficient of drag resulting in a relatively large hydraulic pressure loss/gradient over the length of the fluid treatment system. Still further, the use of a large number of radiation sources in arrangement (ii) can produce vortex effects (these effects are discussed in more detail hereinbelow) resulting in forced oscillation of the radiation sources—such forced oscillation increases the likelihood of breakage of the radiation source and/or protective sleeve (if present).

Accordingly, there remains a need in the art for a fluid treatment system, particularly a closed fluid treatment system which has one or more of the following features:

it can treat large volumes of fluid (e.g., wastewater or drinking water and the like);

it can increase the limit of the maximum admissible velocity through the reactor;

it requires a relatively small "footprint";

it results in a relatively lower coefficient of drag resulting in an improved hydraulic pressure loss/gradient over the length of the fluid treatment system;

it results in relatively lower (or no) forced oscillation of the radiation sources thereby obviating or mitigating breakage of the radiation source and/or protective sleeve (if present);

it can be readily adapted to make use of relatively recently developed so-called "low pressure high output" (LPHO), amalgam and/or other UV emitting lamps while allowing for ready extraction of the lamps from the fluid treatment system for servicing and the like;

it can employ a lamp of a standard length for varying widths of reactors;

it can be readily combined with a cleaning system for removing fouling materials from the exterior of the radiation source(s);

it can be readily installed in a retrofit manner in an existing fluid treatment plant; and it provides relatively improved disinfection performance compared to conventional fluid treatment systems.

SUMMARY OF THE INVENTION

It is an object of the present invention to provide a novel fluid treatment system which obviates or mitigates at least one of the above-mentioned disadvantages of the prior art.

In one of its aspects, the present invention relates to a fluid treatment system comprising:

an inlet;

an outlet;

a fluid treatment zone disposed between the inlet and the outlet, the fluid treatment zone having disposed therein: (i) an elongate first radiation source assembly having a first longitudinal axis, and (ii) an elongate second radiation source assembly having a second longitudinal axis;

wherein the first longitudinal axis and the second longitudinal axis are non-parallel to each other and to a direction of fluid flow through the fluid treatment zone.

In another of its aspects, the present invention relates to a fluid treatment system comprising:

an inlet;

an outlet;

a fluid treatment zone disposed between the inlet and the outlet, the fluid treatment zone having disposed therein an array of radiation source assemblies arranged serially from an upstream region to a downstream region of fluid treatment zone such that: (i) each radiation source assembly has a longitudinal axis transverse to a direction of fluid flow through the fluid treatment zone, (ii) the longitudinal axis of an upstream radiation source assembly is staggered with respect to a downstream radiation source assembly in a direction orthogonal to the direction of fluid flow through the fluid treatment zone to define a partial overlap between the upstream radiation source assembly and the downstream radiation source assembly, and (iii) a flow of fluid has no unobstructed path through the fluid treatment zone.

In another of its aspects, the present invention relates to a fluid treatment system comprising:

an inlet;

an outlet;

a fluid treatment zone disposed between the inlet and the outlet, the fluid treatment zone having disposed therein an array of rows of radiation source assemblies;

each radiation source assembly having a longitudinal axis transverse or parallel to a direction of fluid flow through the fluid treatment zone;

each row comprising a plurality of radiation source assemblies in spaced relation in a direction transverse to the direction of fluid flow through the fluid treatment zone to define a gap through which fluid may flow between an adjacent pair of radiation source assemblies;

all rows in the array being staggered with respect to one another in a direction orthogonal to the direction of fluid flow through the fluid treatment zone such that the gap between an adjacent pair of radiation source assemblies in an upstream row of radiation source assemblies is partially or completely obstructed in the direction of fluid flow by at least two serially disposed downstream rows of radiation source assemblies.

In yet another of its aspects, the present invention relates to a fluid treatment system comprising:

an inlet;

an outlet;

a fluid treatment zone disposed between the inlet and the outlet, the fluid treatment zone having disposed therein an array of radiation source assemblies, each radiation source assembly having a longitudinal axis transverse to a direction of fluid flow through the fluid treatment zone;

the array of radiation source assemblies comprising: a first row of radiation source assemblies, a second row of radiation source assemblies downstream from the first row of radiation source assemblies, a third row of radiation source assemblies downstream from the second row of radiation source assemblies and a fourth row of radiation source assemblies downstream from the third row of radiation source assemblies;

an adjacent pair of radiation source assemblies in the first row defining a first gap through which fluid may flow, a radiation source assembly from the second row partially obstructing the first gap to divide the first gap into a second gap and a third gap, a radiation source assembly from the third row at least partially obstructing the second gap and a radiation source assembly from the fourth row at least partially obstructing the third gap.

In yet another of its aspects, the present invention relates to a fluid treatment system comprising:

an inlet;

an outlet;

a fluid treatment zone disposed between the inlet and the outlet, the fluid treatment zone having disposed therein an array comprising 4 rows radiation source assemblies arranged serially from an upstream portion to a downstream portion of the fluid treatment zone;

each radiation source assembly having a longitudinal axis transverse to a direction of fluid flow through the fluid treatment zone;

wherein: (i) a first pair of rows of radiation source assemblies in the array comprise substantially uniform spacing between adjacent pairs of radiation source assemblies in the row; and (ii) a second pair of rows of radiation source assemblies in the array comprise substantially non-uniform spacing between adjacent pairs of radiation source assemblies in the row.

In addition to the arrayed arrangement of radiation source assemblies described above, it is possible to utilize so-called boundary radiation source assemblies—i.e., radiation source assemblies placed in parallel and in close proximity to the opposed reactor walls. All axes of the boundary radiation source assemblies adjacent to one another, either of the respective outer boundary radiation source assemblies are in the same plane.

Thus, the present inventors have discovered a fluid treatment system having one or more of the following advantages:

it can treat large volumes of fluid (e.g., wastewater, drinking water or the like);

it can increase the limit of the maximum admissible velocity through the reactor;

it requires a relatively small "footprint";

it results in a relatively lower coefficient of drag resulting in an improved hydraulic pressure loss/gradient over the length of the fluid treatment system;

it results in relatively lower (or no) forced oscillation of the radiation sources thereby obviating or mitigating of breakage of the radiation source and/or protective sleeve (if present);

it can be readily adapted to make use of low pressure ultraviolet emitting lamps and relatively recently developed so-called "low pressure high output" (LPHO), amalgam and/or other ultraviolet radiation and photon emitting lamps while allowing for ready extraction of the lamps from the fluid treatment system for servicing and the like;

it can employ a lamp of standard length for varying widths of reactors simply by varying the transverse angle between the lamps;

it can be readily combined with a cleaning system for removing fouling materials from the exterior of the radiation source(s);

it can be readily installed in a retrofit manner in an existing fluid treatment plant; and it provides relatively improved disinfection performance compared to conventional fluid treatment systems (e.g., systems in which the radiation source is disposed such that its longitudinal axis is parallel or orthogonal to the direction of fluid flow through the fluid treatment zone contained within the system).

In one of its general aspects, the present invention relates to a fluid treatment system comprising at least two radiation source assemblies arranged in a novel manner. Specifically, the radiation source assemblies are arranged such that the respective longitudinal axes of the radiation sources therein are in a non-parallel relationship with each other and with respect to the direction of fluid flow through the fluid treatment zone. This is different than conventional fluid treatment systems wherein all lamps are arranged such that the longitudinal axes of the respective radiation sources within the radiation source assemblies are in a parallel relationship and these axes are orthogonal or parallel to the direction of fluid flow.

In a particularly preferred embodiment of this aspect of the invention, the radiation source assemblies are arranged in an array which is generally V-shaped. In this embodiment, it is preferred to have respective banks of radiation source assemblies which are stacked to form the V-shaped arrangement. As will be discussed in more detail below, one of the advantages of orienting the radiation source assemblies in this matter is a significant reduction in forced oscillation of the radiation sources due to vortex effects.

In another of its aspects, the present invention relates to a fluid treatment system wherein the radiation source assemblies are arranged transverse or parallel to the direction of fluid flow through the fluid treatment zone as a series of rows, each row comprising a plurality of radiation sources assemblies spaced apart in a direction orthogonal to the direction of fluid flow through the fluid treatment zone. In one embodiment of this aspect of the invention (also referred to as the "staggered/transverse orientation"), the radiation source assemblies are arranged transverse to the direction of fluid flow through the fluid treatment zone and oriented in a manner whereby, from an upstream portion to a downstream portion of the fluid treatment zone, the radiation source assemblies are staggered in a direction orthogonal to a direction of fluid flow through the fluid treatment zone to define partial overlap between these assemblies. Preferably, the collection of assemblies is arranged such that a flow of fluid has no unobstructed path through the arrangement of radiation source assemblies in the fluid treatment zone. Practically, one may envision this by viewing the inlet of the fluid treatment zone and seeing no clear, unobstructed path through the arrangement of radiation source assemblies in the fluid treatment zone from the inlet to the outlet. In another embodiment of this aspect of the invention (also referred to as the "staggered/parallel orientation"), the radiation source assemblies are arranged parallel to the direction of fluid flow through the arrangement of radiation source assemblies in the fluid treatment zone and oriented in a manner whereby, from an upstream portion to a downstream portion of the fluid treatment zone, the radiation source assemblies are arranged as in the form of at least two serially disposed banks such that rows of radiation source assemblies in an upstream bank are staggered with respect to rows of radiation source assemblies in a downstream bank in a direction orthogonal to the direction of fluid flow through the arrangement of radiation source assemblies in the fluid treatment zone.

In another of its aspects, the present invention relates to a fluid treatment system in which an array of radiation source assemblies are arranged in the fluid treatment zone. The radiation source assemblies are oriented transverse to the direction of fluid flow through the fluid treatment zone. The array of radiation source assemblies includes a first row of radiation source assemblies arranged to define a predetermined spacing between pairs of radiation source assemblies in the row in a direction orthogonal to the direction of fluid flow through the fluid treatment zone. At least two further rows of radiation source assemblies are disposed downstream of the first row of radiation source assemblies. In one preferred embodiment, these downstream rows of radiation source assemblies (i.e., two or more of such rows) combine to fill or occupy the pre-determined spacing between pairs of radiation source assemblies within the column of lamps in the first row—i.e., if one were to view the array of radiation source assemblies from the inlet of the fluid treatment system. In another preferred embodiment, these downstream rows of radiation source assemblies (i.e., two or more of such rows) combine only to partially fill or occupy the pre-determined spacing between pairs of radiation source assemblies within the column of lamps in the first row—i.e., if one were to view the array of radiation source assemblies from the inlet of the fluid treatment system.

In the present fluid treatment system, it is possible to incorporate a so-called transition region upstream and/or downstream of the fluid treatment zone. Preferably, such a transition region serves to funnel or otherwise transition the flow of fluid in a manner such that cross-sectional area of the flow of fluid orthogonal to the direction of fluid flow is: (i) increased (if the transition region is placed upstream of the fluid treatment zone) thereby decreasing fluid flow velocity, or (ii) decreased (if the transition region is placed downstream of the fluid treatment zone) thereby increasing fluid flow velocity.

Throughout the specification, reference is made to terms such as "closed zone", "closed cross-section" and "constrained". In essence, these terms are used interchangeably and are intended to encompass a structure which effectively surrounds the fluid flow in a manner similar to that described in the Maarschalkerweerd #2 Patents (with particular reference to the fluid treatment zone described therein).

Further, as used throughout this specification, the term "fluid" is intended to have a broad meaning and encompasses liquids and gases. The preferred fluid for treatment with the present system is a liquid, preferably water (e.g., wastewater, industrial effluent, reuse water, potable water, ground water and the like). Still further, the terms "rows" and "columns" are used throughout this specification in relation to arrangements of radiation sources and it is to be understood that these terms are used interchangeably.

Those with skill in the art will recognize that there is reference throughout the specification to the use of seals and the like to provide a practical fluid seal between adjacent elements in the fluid treatment system. For example, those of skill in the art will recognize that it is well known in the art to use combinations of coupling nuts, O-rings, bushings and like to provide a substantially fluid tight seal between the exterior of a radiation source assembly (e.g., water) and the interior of a radiation source assembly containing the radiation source (e.g., an ultraviolet radiation lamp).

BRIEF DESCRIPTION OF THE DRAWINGS

Embodiments of the present invention will be described with reference to the accompanying drawings, wherein like numerals designate like elements, and in which.

DETAILED DESCRIPTION OF THE PREFERRED EMBODIMENTS

Figure 1:
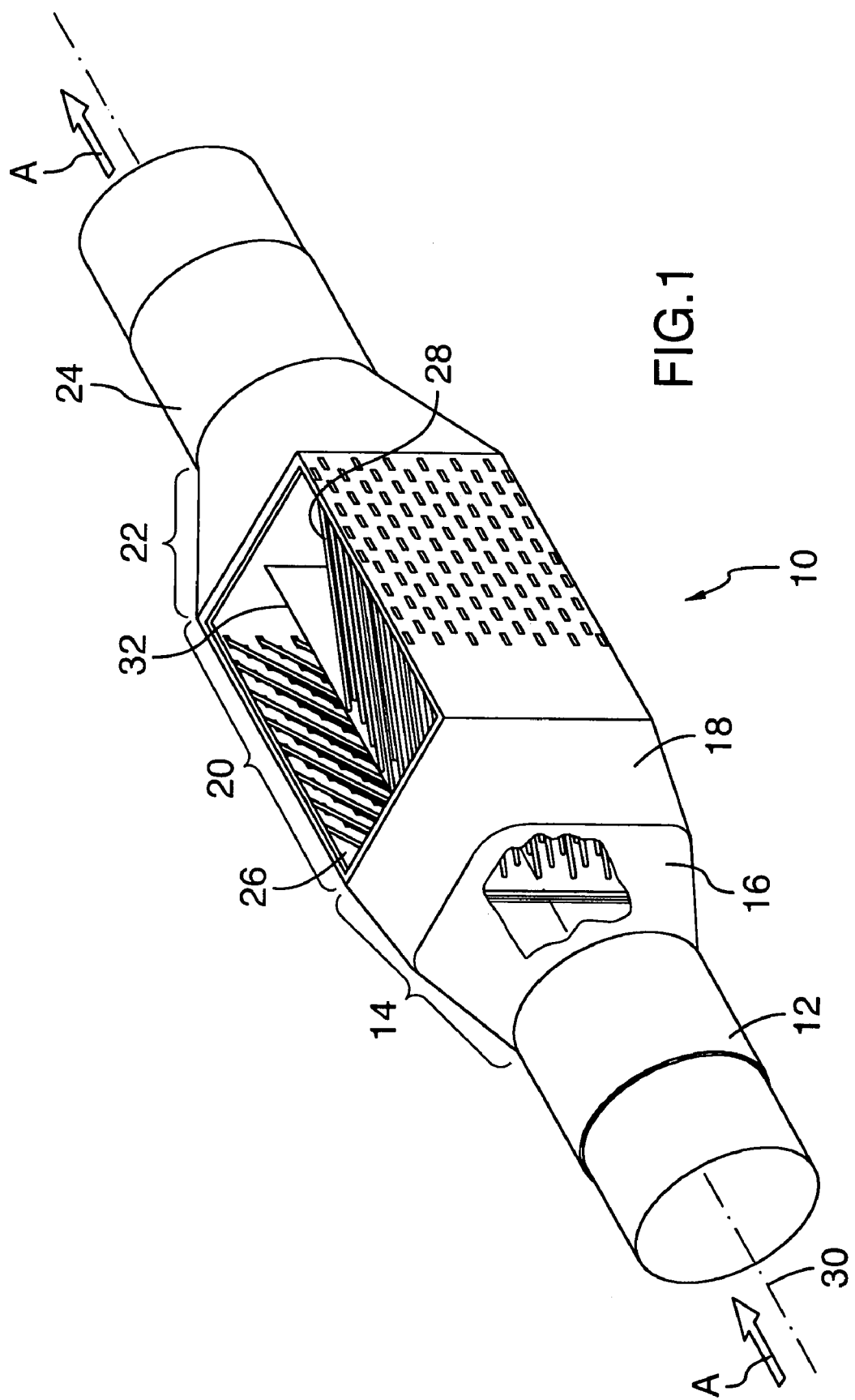
FIG. 1 illustrates, in perspective view, partially cutaway, a schematic of a first embodiment of the present fluid treatment system.

With reference to FIG. 1, there is illustrated a fluid treatment system 10. Fluid treatment system 10 comprises an inlet 12 and an outlet 24. Disposed between inlet 12 and outlet 24 is a fluid treatment zone 20.

Fluid treatment zone 20 is interconnected to inlet 12 by an inlet transition zone 14 comprising a first transition region 16 and intermediate transition region 18. Outlet 24 is interconnected to fluid treatment zone 20 by an outlet transition zone 22.

As illustrated, fluid passes through fluid treatment system 10 (including fluid treatment zone 20) in the direction of arrow A.

As shown, each of inlet 12, inlet transition zone 14, fluid treatment zone 20, outlet transition zone 22 and outlet 24 have a closed cross-section. The use of the term "closed cross-section" is intended to mean an enclosure which bounds a flow of fluid on all sides and/or surfaces.

As shown, inlet 12 and outlet 24 have a circular cross-section much like a conventional pipe arrangement. As further illustrated, fluid treatment zone 20 has a square or rectangular cross-section. Of course it is possible to configure fluid treatment zone 20 to have other cross-sectional shapes.

Disposed in fluid treatment zone 20 is a first bank 26 of radiation source assemblies and a second bank 28 of radiation source assemblies. Each radiation source assembly in banks 26 and 28 is elongate and has a longitudinal axis which is angled with respect to the direction of fluid flow (see arrow A or dashed lined 30 which is a projection of arrow A) through fluid treatment zone 20.

The radiation source assemblies in bank 26 are mounted on one side of fluid treatment zone 20 and have a distal end thereof supported by a support element 32. Similarly, each radiation source assembly in bank 28 has one end mounted on a side of fluid treatment zone 20 and a distal end thereof supported by support element 32.

In the result, the array of radiation source assemblies presented by banks 26 and 28 to the flow of fluid is in the form of an V-shaped configuration with the apex of the "V" being pointed toward the flow of fluid. Of course, the apex of the "V" could be pointed in the opposite direction.

Further, while the distal end of each radiation source assembly in banks 26 and 28 is supported by a single support element 32, other support elements will be apparent of those of skill in the art.

As shown, intermediate transition region 18 serves the purpose of providing a nesting region for the apex of the array of lamps. As such, it is preferred to have the sides of intermediate transition region 18 tapered to a smaller dimension while, in the illustrated embodiment, maintaining the top and bottom at a consistent dimension (this will be discussed further below).

First transition region 16 interconnects intermediate transition region 18 and inlet 12, and serves the purpose of: (i) reducing the dimension of the enclosure, and (ii) transitioning the cross-section shape from a polygon to a circle. Similarly, outlet transition zone 22 serves to reduce the dimension of the enclosure and transition the cross-sectional shape of the enclosure from a circle to a polygon.

The use of inlet transition zone 14 and outlet transition zone 22 also serves to obviate or mitigate hydraulic head loss problems that might occur if dramatic changes in dimensions of the enclosure were cast into the system.

A second embodiment of the present fluid treatment system will now be discussed with reference to FIGS. 2-5. In FIGS. 2-5, elements having the same last two digits as elements appearing in FIG. 1 are attended to denote like elements.

With reference to FIGS. 2-5, there is illustrated a fluid treatment system 100. Fluid treatment system 100 comprises an inlet 112 and an outlet 124. Fluid treatment system 100 further comprises a fluid treatment zone 120.

Inlet 112 is interconnected to fluid treatment zone 120 by an inlet transition zone 114. Fluid outlet 124 is interconnected to fluid treatment zone 120 by an outlet transition zone 122. Inlet transition zone 114 comprises a first transition region 116 and an intermediate transition region 118.

Disposed in fluid treatment zone 120 is a first bank 126 of radiation source assemblies and a second bank 128 of radiation source assemblies. The orientation of the radiation source assemblies in banks 126 and 128 with respect to the direction of fluid flow through fluid treatment zone 120 is similar as that described above with respect to FIG. 1.

As shown, the distal portion of each radiation source assembly in banks 126 and 128 is supported by a support post which is disposed transverse to: (i) the direction of fluid flow through fluid treatment zone 120, and (ii) the longitudinal axis of each radiation source assembly.

Figure 4:
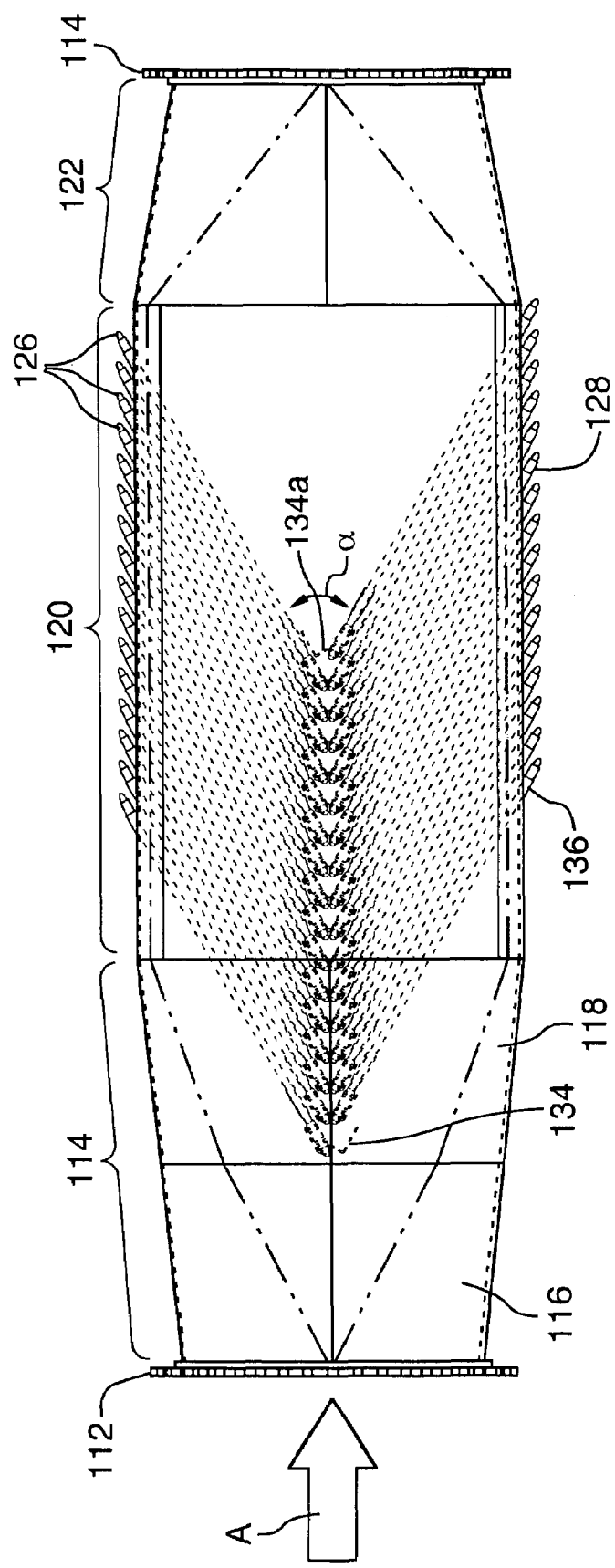
FIG. 4 illustrates a top view (partially cutaway) of the fluid treatment system illustrated in FIG. 2.

As shown, particularly with respect to FIG. 4, a support post 134 is used for each column of radiation source assemblies in banks 126 and 128. As further illustrated FIG. 4, the upstream end of the array of radiation sources comprises a column of radiation source assemblies from bank 126 connected to a support post 134—i.e., there is no similar column of radiation source assemblies from bank 128 supported by the upstream centre support. This arrangement is reversed at a downstream support post 134a. Otherwise, each centre post serves the purpose of supporting a distal portion of radiation source assemblies from one column of each of banks 126 and 128. In some cases support post 134 also acts as a baffle, and likely will act as a protective shield behind which will be parked a cleaning device (described below).

Figure 2:
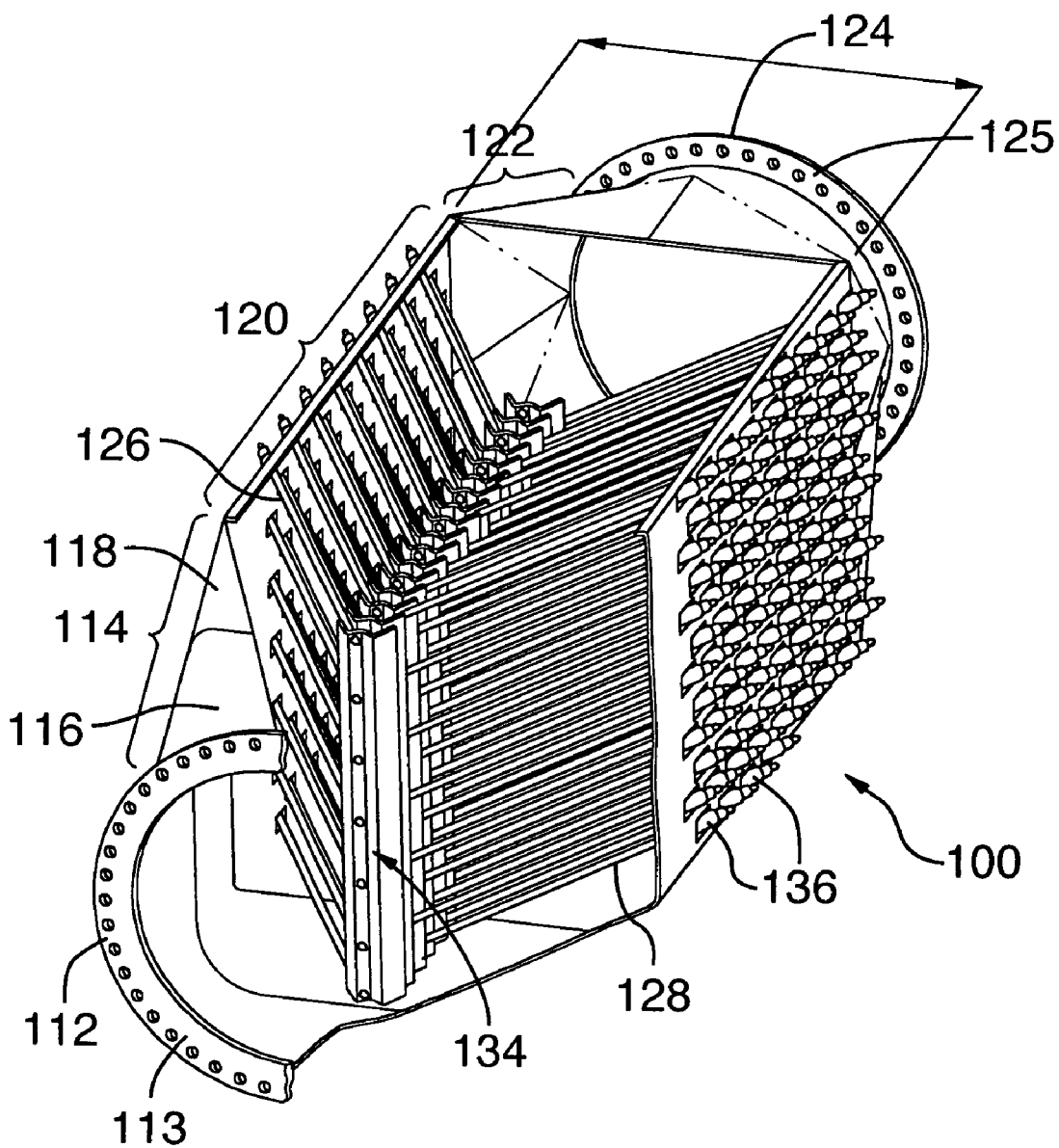
FIG. 2 illustrates a perspective view, partially cutaway of a second embodiment of the present fluid treatment system.
Figure 5:
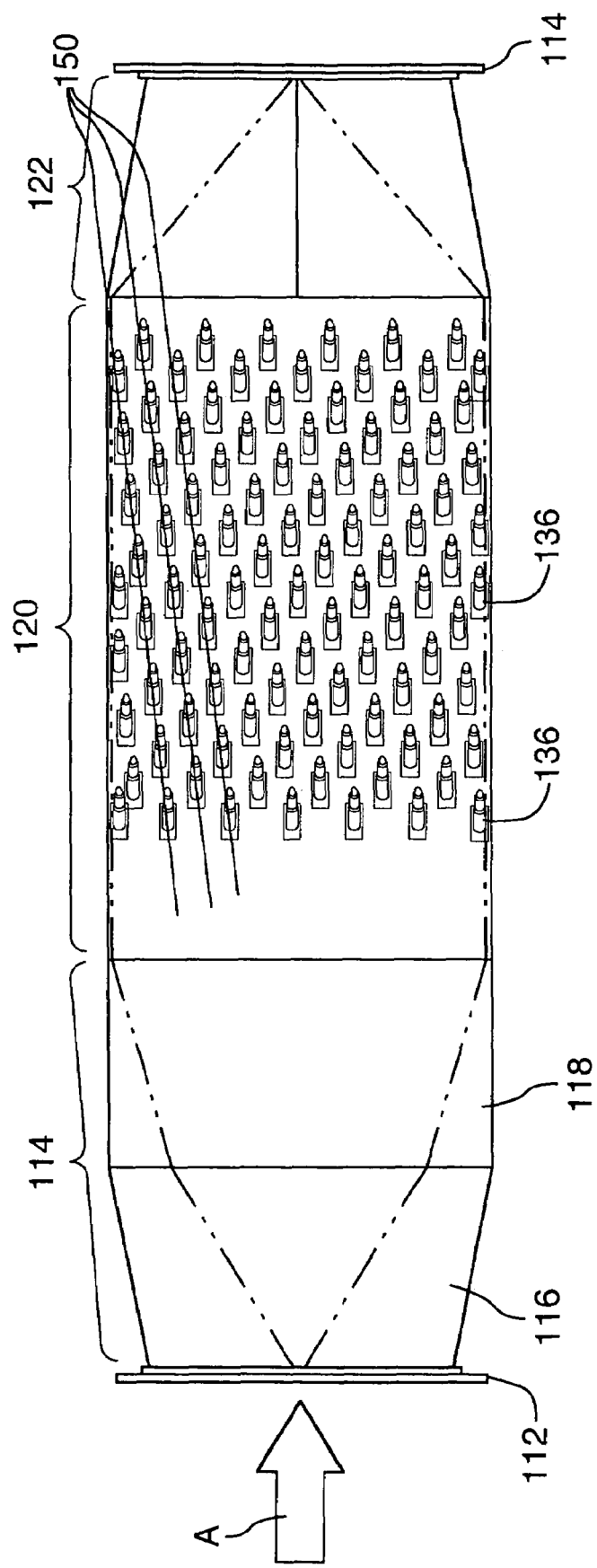
FIG. 5 illustrates a side elevation of the fluid treatment system illustrated in FIG. 2.

With particular reference to FIGS. 2 and 5, it can be seen that mounting sleeves 136 are cast or otherwise secured to the exterior surface of fluid treatment zone 120. The proximal region of each radiation source assembly is received in mounting sleeves 136 and a fluid type seal (not shown) can be achieved in a conventional manner.

As further illustrated in FIGS. 2-5, inlet 112 and outlet 124 can be adapted to have a suitable standard flange element 113 and 125, respectively. This facilitates insulation of fluid treatment system 100 in conventional piping. For example, it is possible for flange elements 113 and 125 to be configured for conventional piping sizes between, for example, 12 inches and 72 inches.

Figure 3:
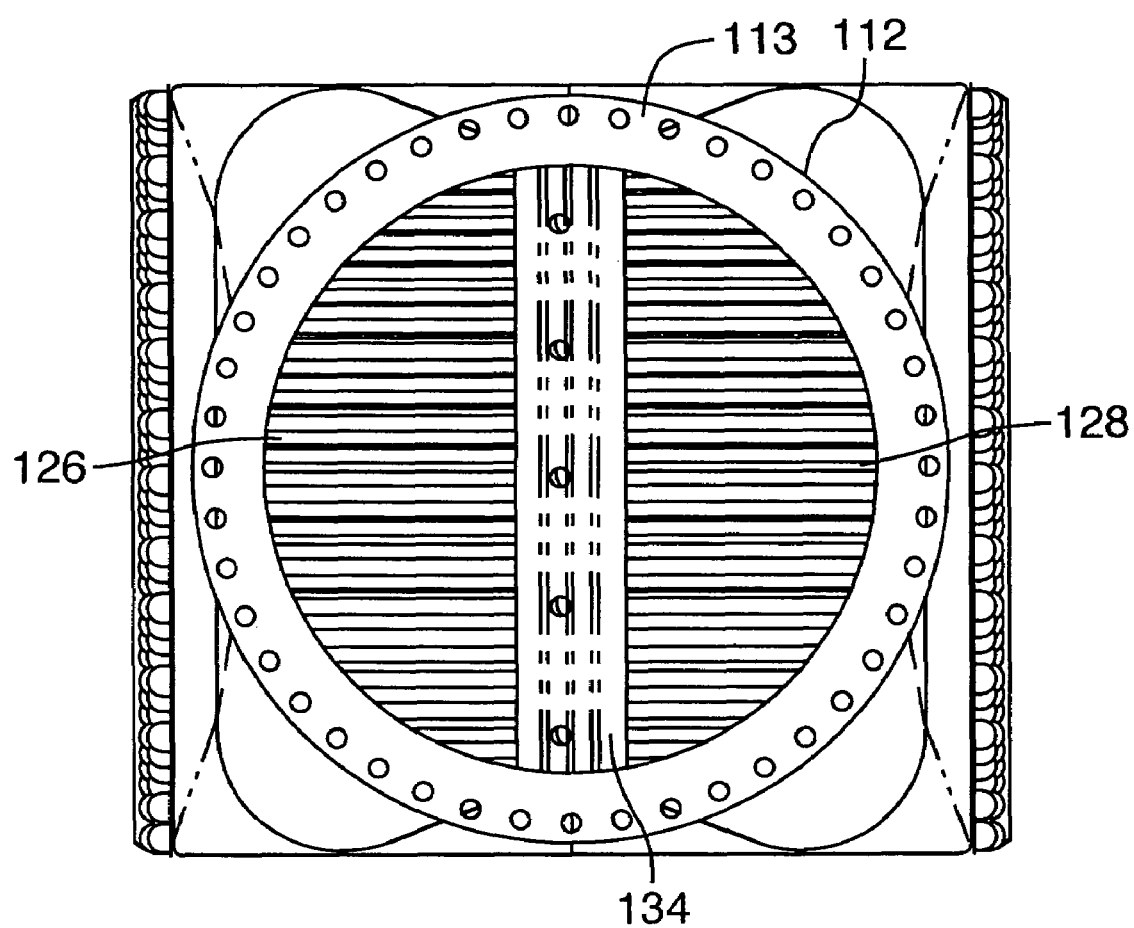
FIG. 3 illustrates an end view from the inlet of the fluid treatment system illustrated in FIG. 2.

With particular reference to FIG. 3, it will be seen that banks 126 and 128 are arranged as an array of radiation source assemblies that present an obstruction which completely fills fluid treatment zone 120 when the fluid treatment zone 120 is viewed through inlet 112. In other words, there is no apparent path by which fluid can pass through fluid treatment zone 120 without being forced to detour around a radiation source assembly in banks 126 and/or 128. This being the case, the axis of each radiation source assembly can be seen by an observer looking along the direction of fluid flow through fluid treatment zone 120.

This effect is created by partially staggering the orientation of radiation source assemblies in banks 126 and 128. For example, with reference to FIG. 5, it can be seen that, proceeding lengthwise along fluid treatment zone 120, there is partial overlap of an upstream radiation source assembly with a downstream radiation source assembly in a successive manner—see, for example, lines 150 in FIG. 5 which illustrate such a gradual staggering of radiation source assemblies in each of banks 126 and 128. In other words, a downstream radiation source assembly is partially exposed and partially obscured by an adjacent upstream radiation source assembly. Thus, it can be seen that the complete obstruction of the cross-sectional area the section of fluid treatment zone 120 (i.e., the section in which banks 126 and 128 are disposed) discussed above is not achieved by staggering of two successive columns of radiation source assemblies in banks 126 and 128 such that a downstream radiation source assembly fills the space between a pair of upstream radiation source assemblies. Rather, in this embodiment, three or more columns of such radiation source assemblies are oriented, in combination, to achieve the complete obstruction.

Preferably, each radiation source assembly preferably comprises of an elongate radiation source (e.g. an ultraviolet radiation lamp such as a low pressure high output ultraviolet radiation lamp) disposed within a protective sleeve (e.g. made from a radiation transparent material such as quartz and the like). In some case it may be possible (and preferred) to utilize a radiation source without a protective sleeve (e.g., photon emitting lamps without a protective sleeve).

As can be seen, particularly with reference to FIG. 5, intermediate region 118 of inlet transition zone 114 has a transverse direction the same as fluid treatment zone 120. The sides of intermediate region 118 of inlet transition zone 114 are tapered as shown in FIG. 4. This arrangement allows for the tapering transition on the one hand while leaving adequate room for the apex of the array of radiation sources on the other hand.

The radiation source assemblies in banks 126 and 128 have longitudinal axes which are angled with respect to the direction of fluid flow (arrow A) through fluid treatment zone 120. The result is an apex-shape orientation of radiation source assemblies in banks 126 and 128 as clearly seen in, for example, FIG. 4. The angle α between the respective longitudinal axes of radiation source assemblies in banks 126 and 128 is preferably in the range of from about 15° to about 170°, more preferably from about 35° to about 120°, even more preferably from about 50° to about 120°, most preferably from about 60° to about 90°. It will be appreciated by those of skill in the art that, with a fixed length radiation source, the angle will determine the cross sectional area of the reactor. Further, although not illustrated specifically in the drawings herein, it is preferred and desirable to incorporate in the present fluid treatment system a cleaning device for removing fouling materials from the exterior of the radiation source assemblies in banks 126 and 128.

Figure 9:
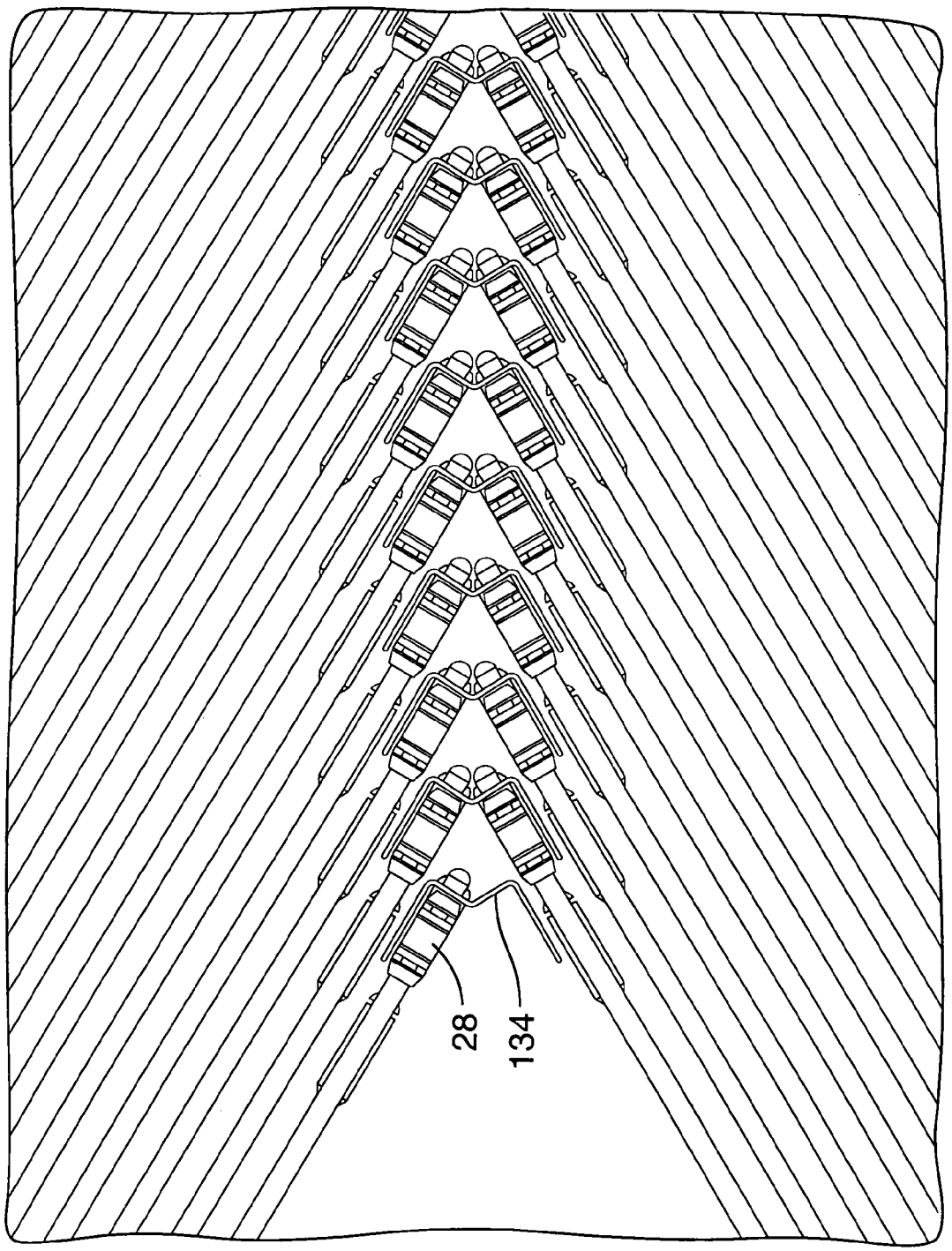
FIG. 9 illustrates a top view of an array of radiation source assemblies incorporating a cleaning device for removing fouling materials from the exterior of the assemblies.

An example of incorporating a cleaning device in the present fluid treatment system is illustrated schematically in FIG. 9. As shown, it is possible to incorporate the cleaning device as a sleeve which travels in a reciprocal manner over the exterior of the radiation source assemblies. As shown, a cleaning device 28 is provided for each radiation source assembly in the form of a movable sleeve. In the illustrated embodiment, cleaning device 28 is "parked" such that it is downstream of support post 134. The nature of cleaning device 28 is not particularly restricted. See, for example, U.S. Pat. No. 6,342,188 [Pearcey et al.] and U.S. Pat. No. 6,646,269 [Traubenberg et al.], both assigned to the assignee of the present invention.

Figure 6:
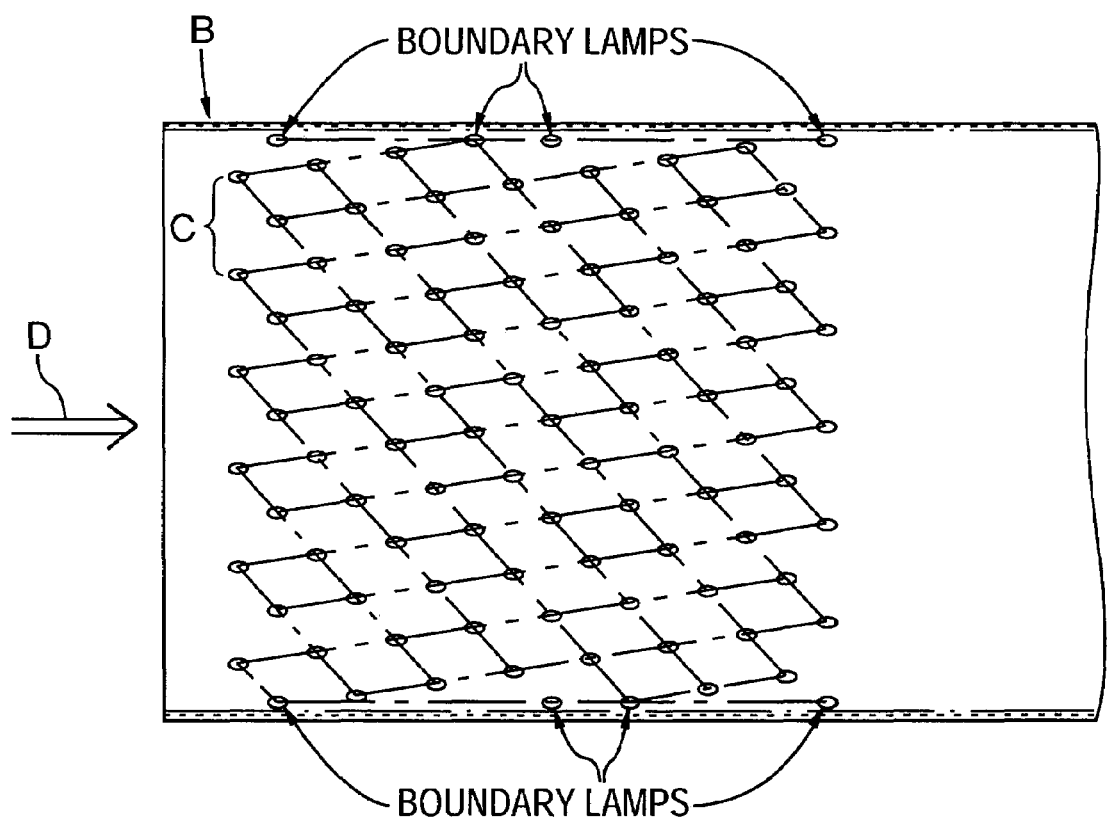
FIG. 6 illustrates a schematic side elevation of orientation of radiation source assemblies in a third embodiment of the present fluid treatment system.

With reference to FIG. 6, there is illustrated the side elevation, in schematic, of an arrangement of radiation source assemblies. Generally, this arrangement is the same as the V-shaped configuration discussed above. As shown, there is a row B of 6 radiation source assemblies disposed vertically in the fluid treatment zone. Between each pair of radiation source assemblies in row B, there is a pre-determined spacing C.

As illustrated, radiation source assemblies downstream of row B are arranged in a manner whereby more than two subsequent downstream vertical rows of radiation source assemblies are required to partially obscure pre-determined spacing C. In other words, if one were to view the array of radiation source assemblies along arrow D the flow of fluid through pre-determined spacing C would be obstructed as a result of the arrangement of at least two rows of radiation source assemblies downstream of row B. It will be appreciated by those of skill in the art that, with a relatively large enough number of rows B, the staggered radiation source assemblies per row can completely obstruct the line of vision through the staggered array whereas with fewer radiation source assemblies, the line of sight would not be completely obstructed.

As shown, the array of radiation source assemblies includes a quartet of boundary lamps disposed in the same plain at the outer edges of the staggered array, in this embodiment, of the fluid treatment zone. As further illustrated, the array of radiation source assemblies is arranged to define repeating pattern consisting of a parallelogram containing four radiation source assemblies.

Figure 7:
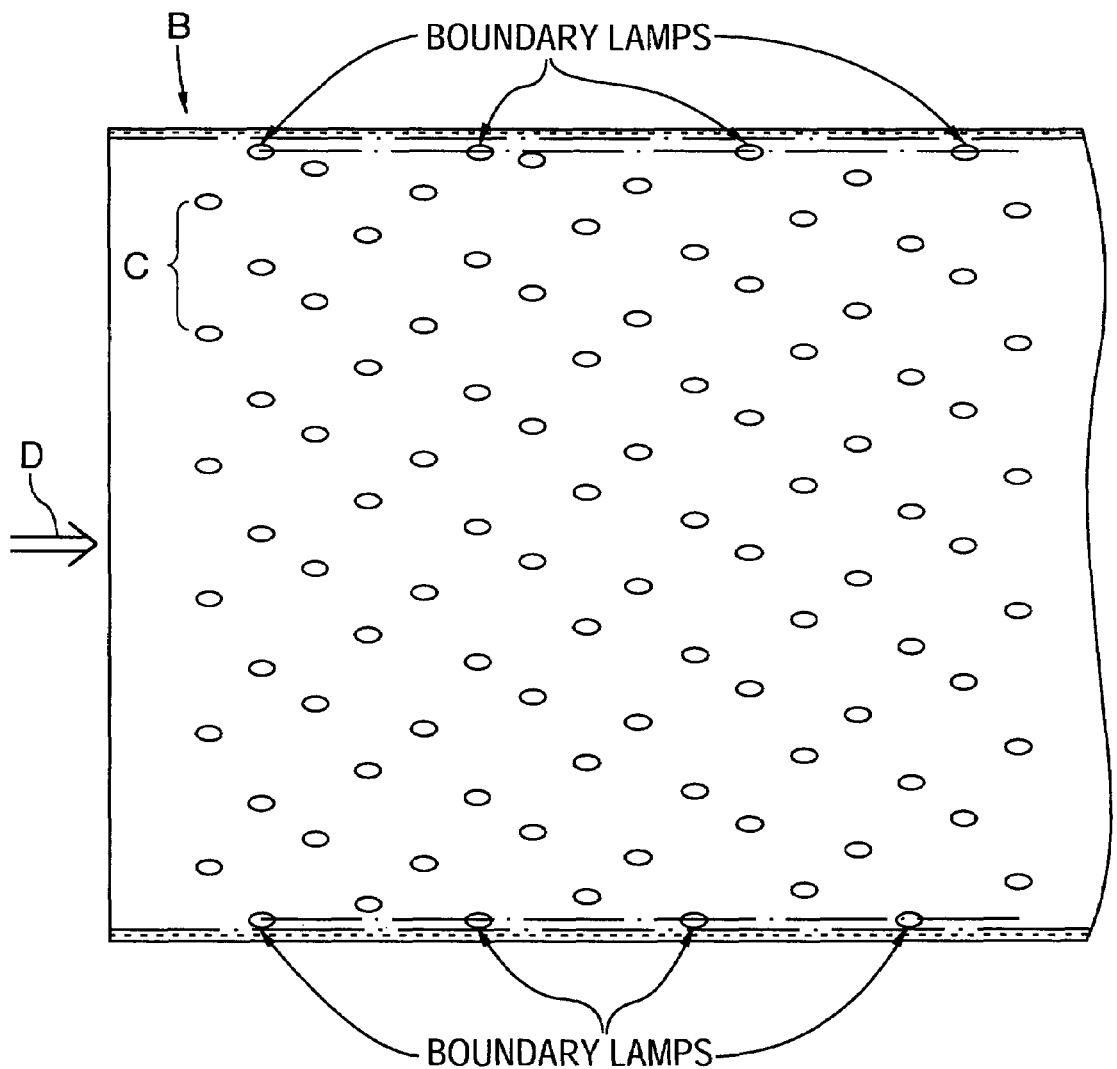
FIG. 7 illustrates a schematic side elevation of orientation of radiation source assemblies in a fourth embodiment of the present fluid treatment system.

FIG. 7 illustrates a schematic similar to the one shown in FIG. 6 with the exception that the staggering of the radiation source assemblies is different from that shown in FIG. 6. Specifically, it will be seen that the parallelogram repeating pattern referred to above with reference to FIG. 6 does not appear in the arrangement shown in FIG. 7. Otherwise, FIG. 7 does illustrate the use of boundary lamps and the staggering of subsequent rows of radiation source assemblies such that the gap between pairs of radiation source assemblies in the first row is effectively filled by more than two subsequent rows as one views the array of radiation source assemblies from one end of the fluid treatment zone.

Figure 8A:
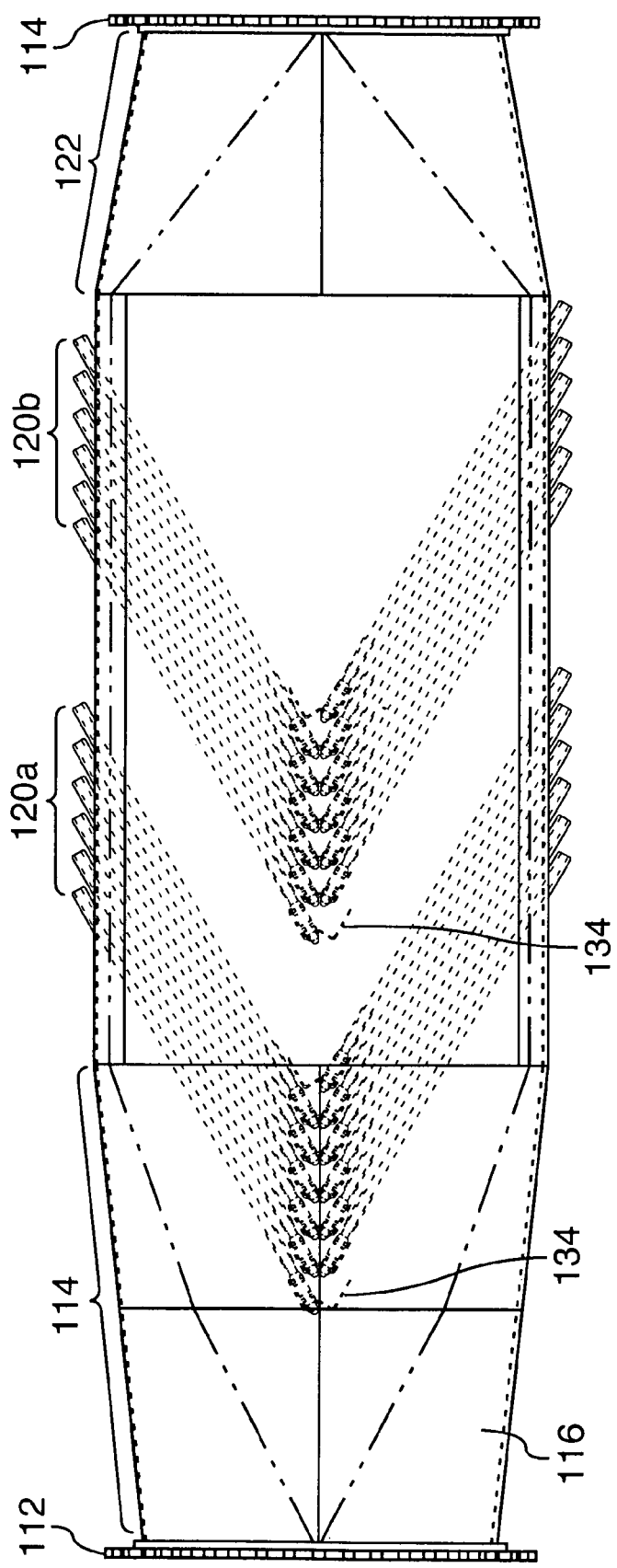
FIG. 8a illustrates a top view (partially cutaway) of a fifth embodiment of the present fluid treatment system.

FIG. 8a is a schematic similar to that shown in FIG. 4 with the exception that two arrays 120a and 120b are used in the fluid treatment zone. As shown, each of array 120a and array 120b is a V-configuration similar to that shown in FIGS. 1-4 described above.

Figure 8B:
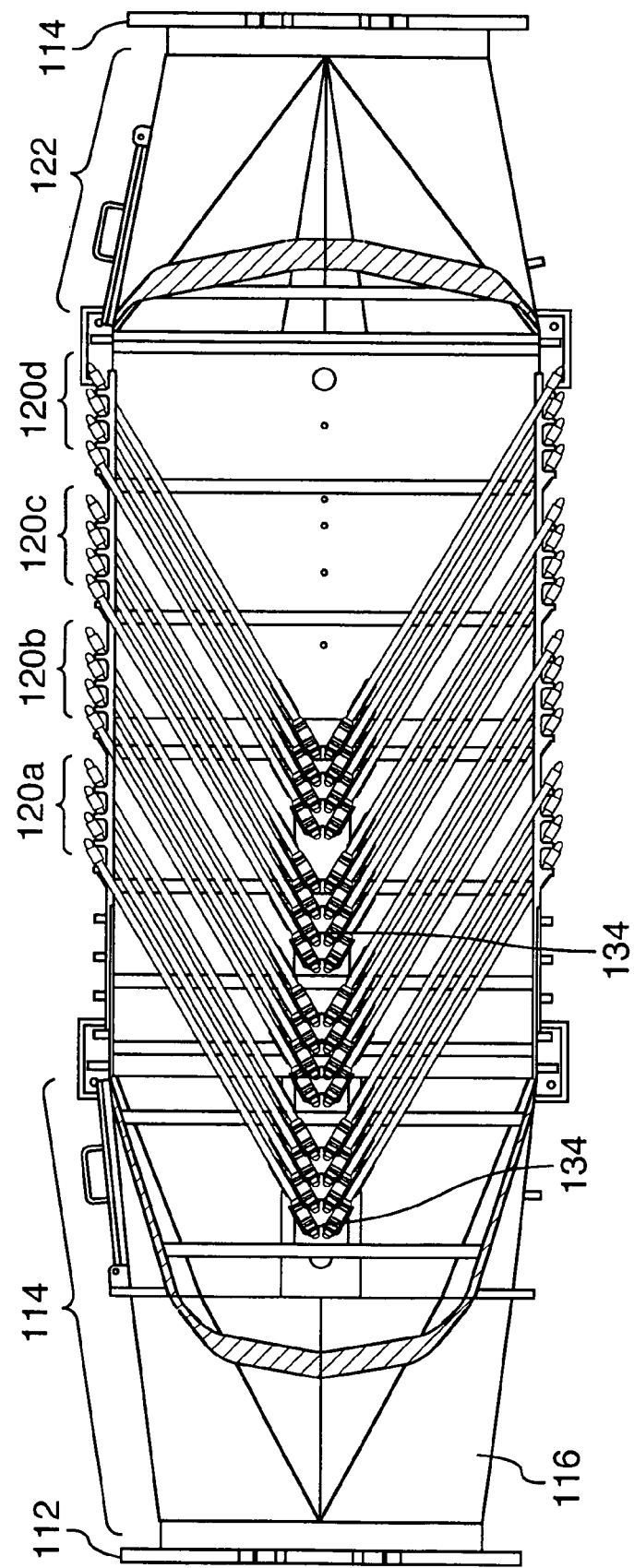
FIG. 8b illustrates a top view (partially cutaway) of a sixth embodiment of the present fluid treatment system.

FIG. 8b is a schematic similar to that shown in FIG. 4 with the exception that four arrays 120a, 120b, 120c and 120d are used in the fluid treatment zone. As shown, each of array 120a, 120b, 120c and 120d is a V-configuration similar to that shown in FIGS. 1-4 described above. Preferably, each array 120a, 120b, 120c and 120d is arranged as described below with reference to FIG. 16. In FIG. 8b, it is preferred that the spacing between adjacent arrays 120*a*, 120*b*, 120*c* and 120*d* is equal to the spacing between adjacent pairs lamps in a column of lamps in an array (e.g., dimension X in FIG. 16).

Figure 10:
FIG. 10 illustrates vortices generated as fluid flows passes a radiation source assembly of a prior art fluid treatment system.

With reference to FIG. 10, there is shown, in schematic, a radiation source assembly E which is disposed such that its longitudinal axes is orthogonal to the direction of fluid flow shown by arrow A—such an orientation is known from the prior art. As will be understood by those of skill in the art, this orientation of radiation source assembly E presents a circular cross-section to the direction of fluid flow shown by arrow A. Consequently, vortices are generated downstream of radiation source assembly E which are random and wide-angled. The result of this is forced oscillation of radiation source assembly E and/or other radiation source assemblies in the vicinity of radiation source assembly E which can lead to breakage thereof.

Figure 11:
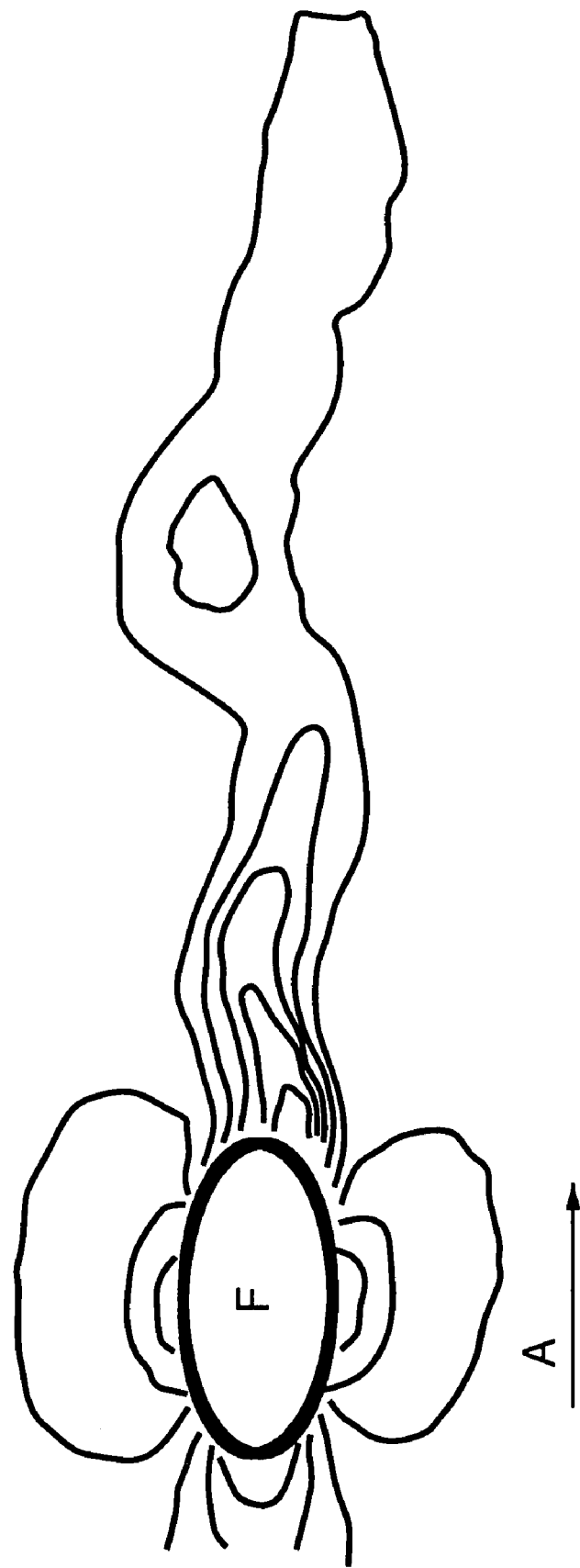
FIG. 11 illustrates vortices generated as fluid flows passes a radiation source assembly of a fluid treatment system in accordance with the present invention.

With reference to FIG. 11, there is shown, in schematic, a radiation source assembly F orientated in the manner described above with reference to FIGS. 1-4. In this orientation, radiation source assembly F presents an oval or ellipse cross-section to the direction of the flow of fluid depicted by arrow A. Consequently, vortices downstream of radiation source assembly F are more regular and less likely to create the forced oscillation disadvantages that can result in breakage of the radiation source assembly.

With reference to FIGS. 12-15, there is illustrated schematic end views (i.e., view thorough the fluid treatment zone) of a number of embodiments of the staggered/parallel orientation referred to above. In FIGS. 12-15, reference is made to "First", "Second" and "Third" (FIG. 13-15) when describing a "Bank" of radiation source assemblies. These terms are intended to denote serial placement of a given "Bank" in a direction from an upstream portion to a downstream portion of the fluid treatment zone.

Figure 12:
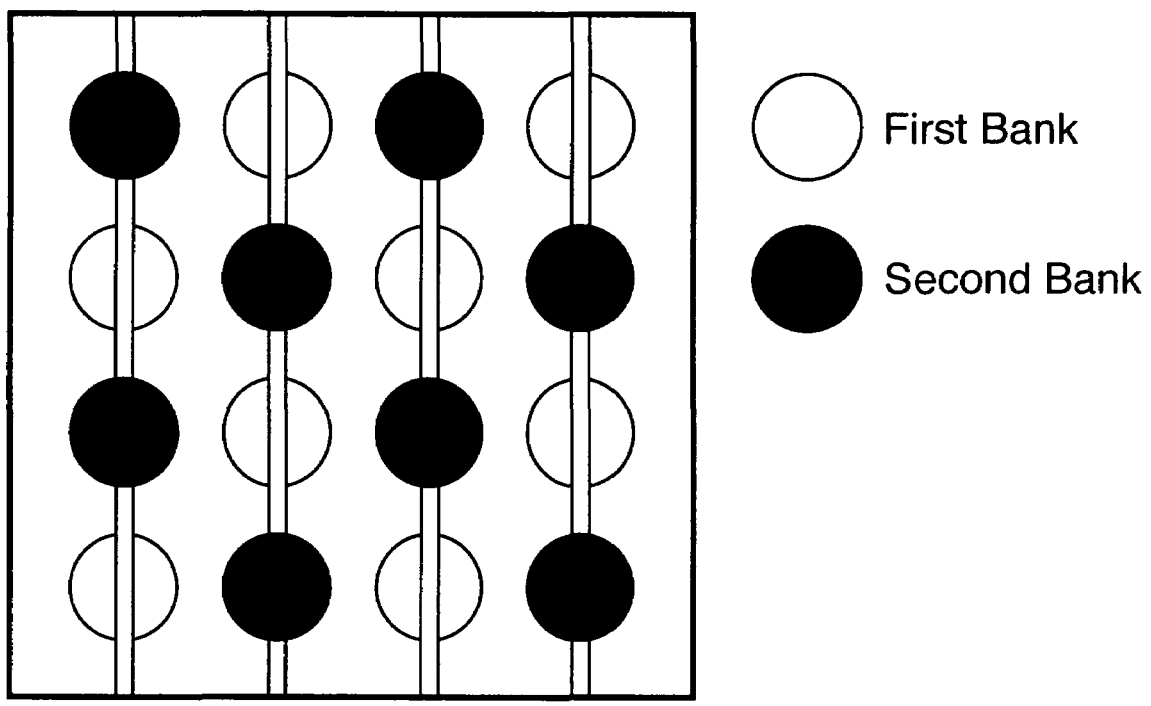
FIGS. 12-15, there is illustrated schematic end views (i.e., viewed through the fluid treatment zone) of a number of embodiments of the staggered/parallel orientation referred to above.

Thus, with reference to FIG. 12, it will be seen that the rows of radiation source assemblies in the "First Bank" are staggered in two respects: (i) there is a stagger with respect to a downstream (or upstream) "Second Bank" of radiation source assembles, and (ii) there is a stagger between adjacent rows of radiation source assemblies in the "First Bank". The arrangement of radiation source assemblies shown in FIG. 12 is particularly well suited for application in fluid treatment systems such as those described in the Maarshalkerweerd #2 Patents.

Figure 13:
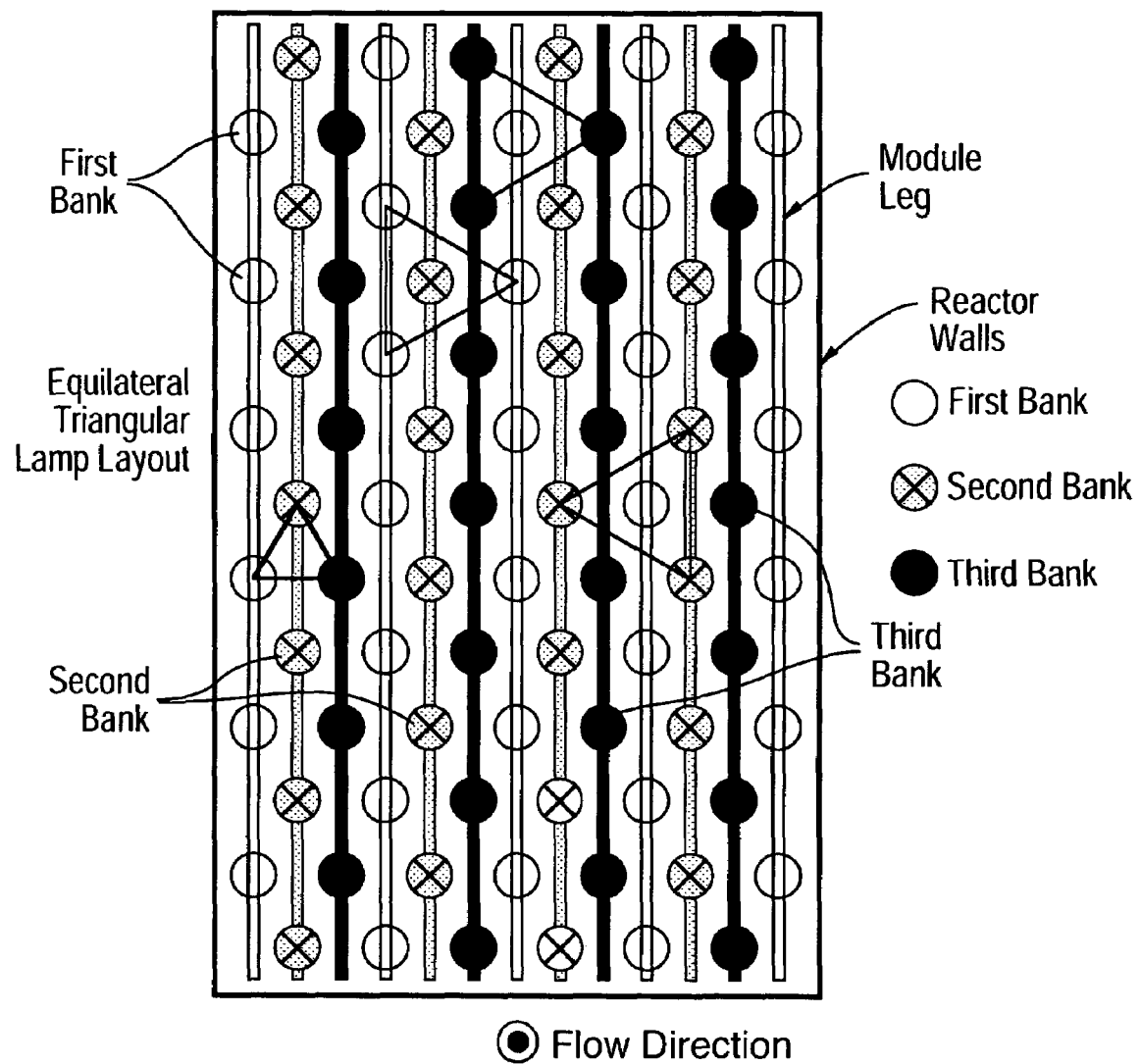

With reference to FIG. 13, there is illustrated another schematic arrangement of radiation source assemblies in accordance with the staggered/parallel orientation referred to above. The arrangement of radiation source assemblies shown in FIG. 13 is particularly well suited for application in open channel fluid treatment systems such as those described in the Maarshalkerweerd #1 Patents. As shown, the arrangement of radiation source assemblies comprises a First Bank, a Second Bank and a Third Bank. It will be seen that, in an end view, for an adjacent trio of rows of radiation source assemblies in the First Bank, the Second Bank and the Third Bank, each of the First Bank and the Third Bank is: (i) staggered with respect to the Second Bank, and (ii) non-staggered respect to the other. The resulting orientation of radiation may be characterized by: (i) an equilateral triangle though the axis of radiation source assemblies in adjacent rows of the same Bank, and (ii) an equilateral triangle though the axis of radiation source assemblies in an adjacent trio rows of the First Bank, the Second Bank and the Third Bank.

Figure 14:
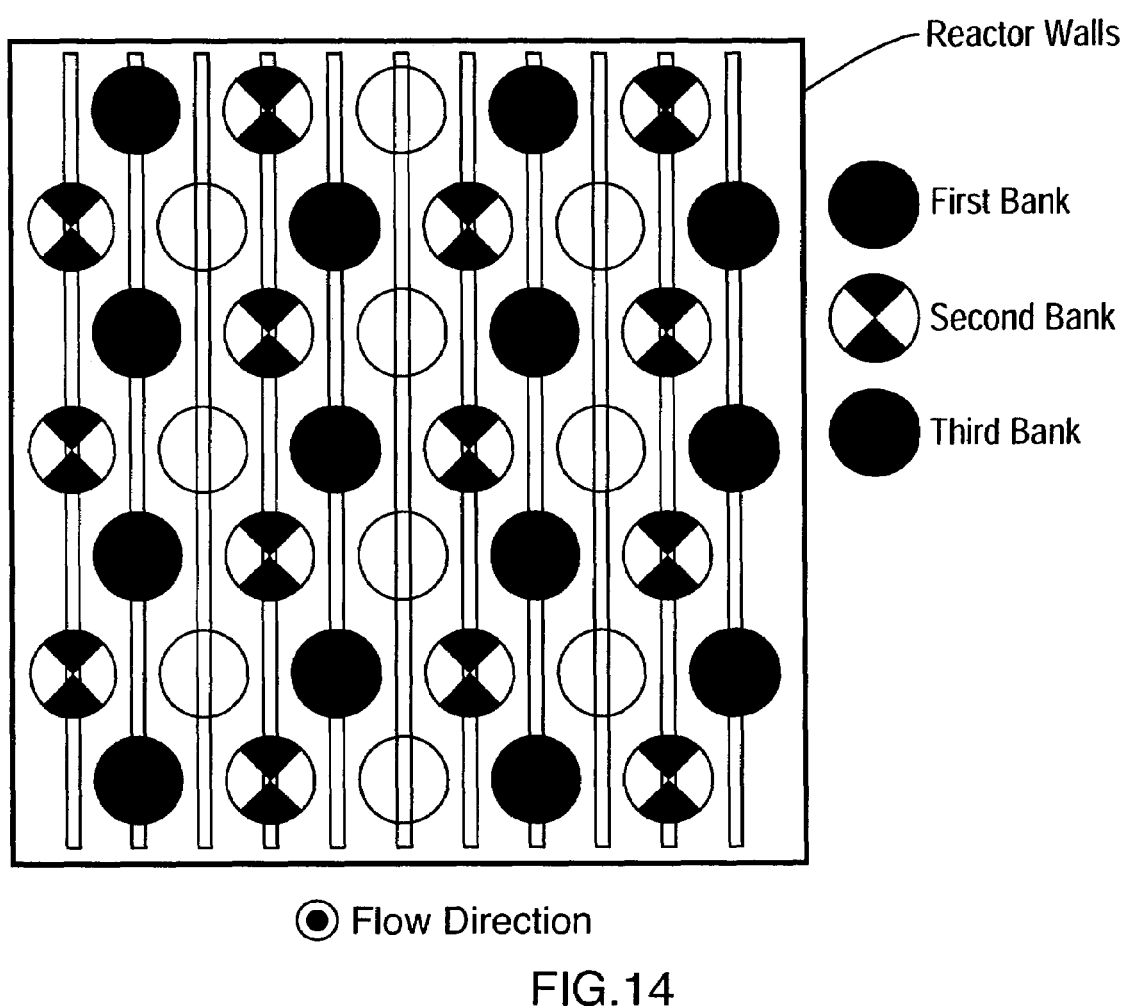
Figure 15:
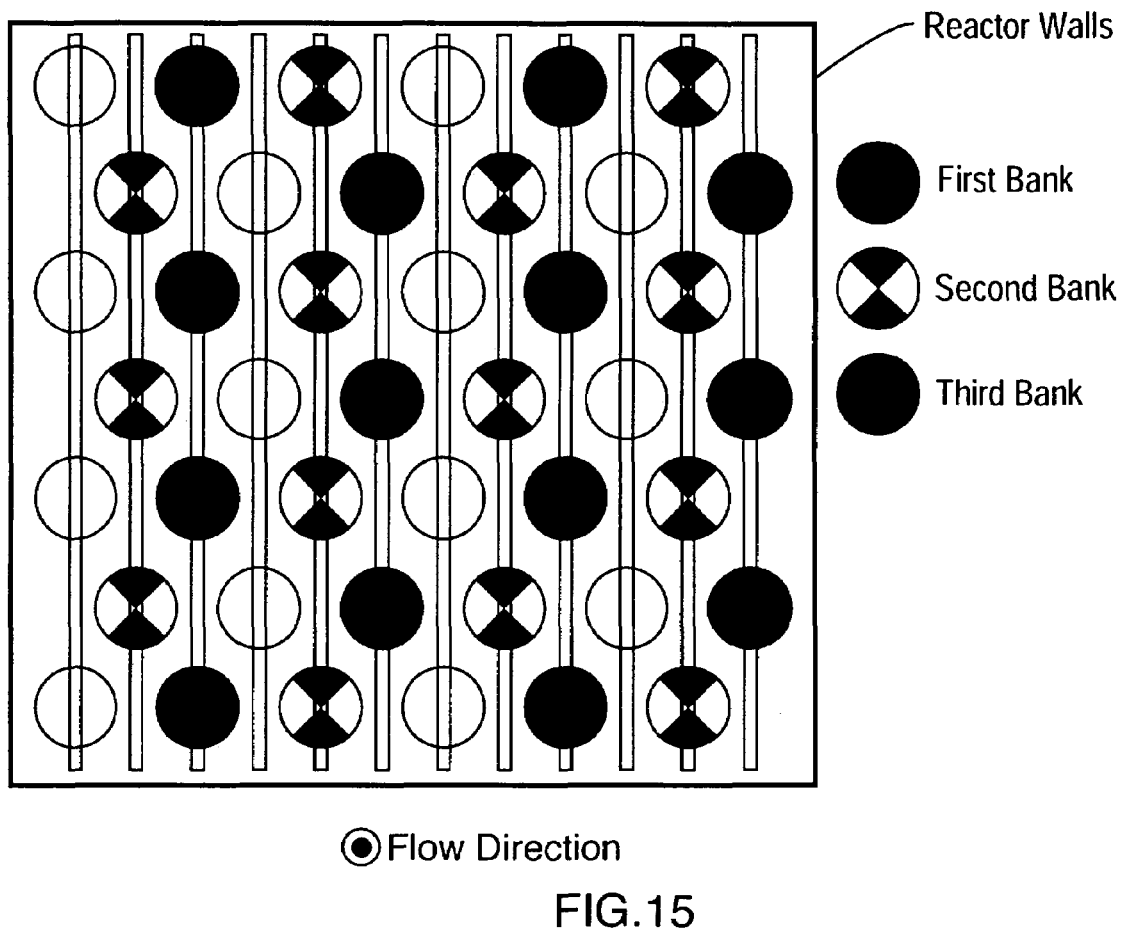

With reference to FIGS. 14 and 15, there are illustrated schematic views of arrangements of radiation source assemblies similar to that discussed above with reference to FIG. 13. In FIG. 13, from the left hand reactor wall, the positioning of rows is: First Bank followed by Second Bank followed by Third Bank. In FIG. 14, from the left hand reactor wall, the positioning of rows is: Second Bank followed by Third Bank followed by First Bank. In FIG. 15, from the left hand reactor wall, the positioning of rows is: Second Bank followed by First Bank followed by Third Bank.

Figure 16:
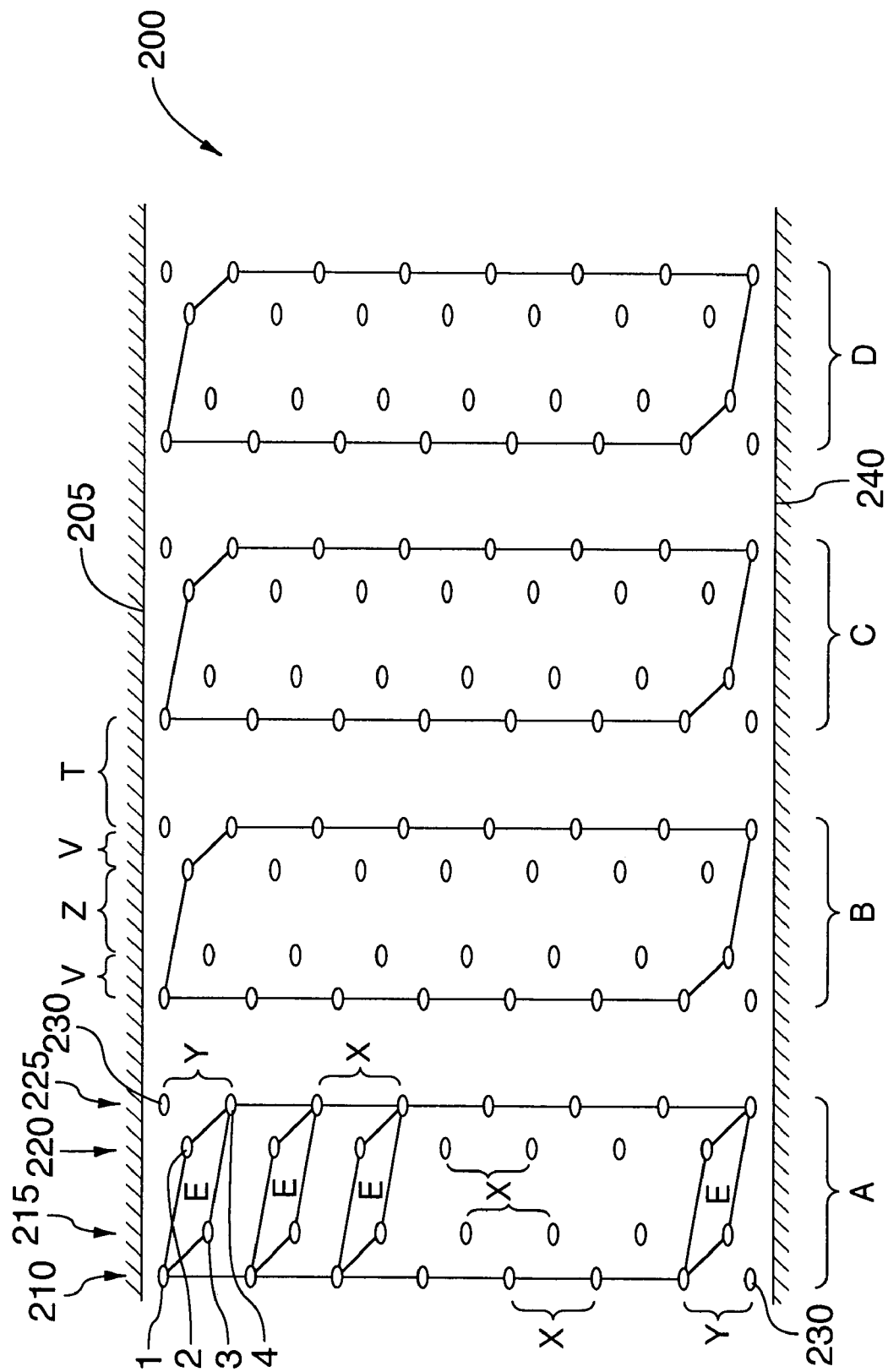
FIG. 16 illustrates a schematic side elevation of orientation of radiation source assemblies in a highly preferred embodiment of the present fluid treatment system.

With reference to FIG. 16, there is illustrated a highly preferred arrangement of radiation source assemblies for use in the present fluid treatment system. Thus, in FIG. 16, there is illustrated a schematic arrangement (e.g., specific details support, electrical connection and sealing of the radiation source assemblies has been omitted for clarity) of the radiation source assemblies shown in a side elevation of the fluid treatment system. Each oval in FIG. 16 denotes an opening in a wall of the fluid treatment system through which an end of the radiation soured assembly would emanate. It is preferred to arrange the radiation source assemblies in a manner such as illustrated above with reference to any of FIGS. 1-4, 8*a* and 8*b*.

With continued reference to FIG. 16, there is illustrated a fluid treatment system 200 comprising, in a preferred embodiment, an enclosed (or closed) fluid treatment zone having a reactor ceiling 205 and a reactor floor 240. Disposed between reactor ceiling 205 and reactor floor 240 are four modules A, B, C and D of radiation source assemblies. Modules A, B. C and D are substantial the same. Those with skill in the art will appreciate that, while four modules are illustrated in FIG. 16, it is possible to use fewer or greater then four depending on the volume of fluid being treated, the quality of fluid being treated and other factors within the purview of a person skilled in the art.

Each of modules A, B, C and D comprises four rows 210, 215, 220 and 225. As shown, rows 215 and 220 each comprise a series of radiation source assemblies where each adjacent pair of radiation source assemblies in each row are spaced apart in a substantially uniform manner. Specifically, the distance between all adjacent pairs of radiation source assemblies in row 215 is X as is the distance between all adjacent pairs of radiation source assemblies in row 220.

With reference to rows 210 and 225, it will be seen that most of the pairs of adjacent radiation source assemblies are equally spaced and, in a preferred embodiment, the spacing is X as shown with respect of rows 215 and 220. However, rows 210 and 225 also contain a pair of radiation source assemblies with a spacing Y that is less then spacing X used elsewhere in rows 210 and 225.

As will be seen with reference to module A, a quartet of radiation source assemblies including a single radiation source assembly from each of rows 210, 215, 220 and 225 is arranged to define a parallelogram repeating unit E. Parallelogram repeating unit E comprises all of the radiation source assemblies in module A except the pair of boundary radiation source assemblies 230. Those with skill in the art will appreciate that it is possible to use parallelogram repeating pattern E to scale up or scale down module A (or one or more modules B, C and D) depending on factors such as the volume of fluid being treated and the like.

Another feature of module A is the so-called stagger order of the radiation source assemblies appearing in the parallelogram repeating unit E. As shown, progressing from reactor ceiling 205 to reactor floor 240, for a given parallelogram repeating pattern E, the following is the order of rows from which the radiation source assembly is derived: 210, 220, 215 and 225. In other words, for a given parallelogram repeating unit E, the sequence of rows progressing from an upstream portion of the fluid treatment zone to a downstream portion of the fluid treatment zone (i.e., 210, 215, 220 and 225) differs from the sequence of rows progressing from reactor ceiling 205 to reactor floor 240 (i.e., 210, 220, 215 and 225). This results in the parallelogram repeating unit E and provides advantageous in the ability to efficiently treat fluid passing through fluid treatment system 200.

Specifically, this so-called stagger order allows for scalability and modulation of the power used to operate the fluid treatment system. By this it is meant that, using a stagger order such as parallelogram repeating pattern E, it is possible to lower the power consumption or even turn off of the power to certain rows of radiation source assemblies within a given module (e.g., one, some or all of modules A, B, C and D) to account for factors such as fluid transmittance, type and/or concentration of a particular contaminant and the like. For example, it is possible to operate the radiation source assemblies in rows 210 and 215 at full power while lowering or turning off the power to the radiation source assemblies in rows 220 and 225. This allows for advantageous fining tuning of the overall power consumption of the fluid treatment system (power consumption is usually the single largest operating expense associated with the fluid treatment system).

Such fine tuning would be difficult to achieve if the sequence of rows progressing from an upstream portion of the fluid treatment zone to a downstream portion of the fluid treatment zone (i.e., 210, 220, 215 and 225) was the same as the sequence of rows progressing from reactor ceiling 205 to reactor floor 240 (i.e., 210, 215, 220 and 225). In this situation, to modify power consumption, it would be necessary to turn off entire modules within the fluid treatment zone resulting in relatively uneven fluid treatment.

With further reference to FIG. 16, it can be seen that the spacing V between rows 210 and 215 is the same as the spacing between rows 220 and 225. It can be further seen that the spacing Z between rows 215 and 220 is greater that spacing V. In certain cases, it may be desirable for spacing V and spacing Z to be substantially the same.

Still further, there is a spacing T between adjacent modules A, B, C and D. It can be seen that spacing T is greater than spacing V. In certain cases, it may be desirable for spacing V and spacing T to be substantially the same.

Further, in certain cases, it may be desirable for spacing V, spacing Z and spacing T to be substantially the same.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, while the illustrated embodiments described above with reference to the accompanying drawings relate to a fluid treatment system comprising a fluid treatment zone having a closed cross-section, it is possible and, in some cases, preferred to implement the present fluid treatment system with a fluid treatment zone having an open or other non-closed cross-section (e.g., in an open channel system such as is described in the Maarschalkerweerd #1 Patents referred to above). Still further, it is possible and, in some cases, preferred to implement the present fluid treatment system with a fluid treatment zone having an semi-enclosed cross-section (e.g., such as is described in the Maarschalkerweerd #2 Patents referred to above). Still further, it is possible and, in some cases, preferred to implement the present fluid treatment system with a fluid treatment zone that employs so-called "hybrid" radiation source modules (e.g., such as described in United States patent application publication No. 2002/113021 [Traubenberg et al.] or in International Publication Number WO 04/000,735 [Traubenberg et al.]). as stated above, it is possible to incorporate a mechanical or chemical/mechanical cleaning system to remove fouling materials from the exterior of the radiation source assemblies as described various published patent applications and issued patents of Trojan Technologies Inc. Still further, a variety of conventional sealing systems made of a variety of materials may be used in the present fluid treatment system. The selection of sealing materials and the placement thereof to obtain a sufficient seal is not particularly restricted. Still further, it is possible to modify the illustrated embodiments to use weirs, dams and gates upstream, downstream or both upstream and downstream to optimize fluid flow upstream and downstream of the fluid treatment zone defined in the fluid treatment system of the present invention. Still further, it is possible to modify the illustrated embodiments to include sloped and/or stepped channel surfaces such as is disclosed in International Publication Number WO 01/66469 [Brunet et al.]. Still further, it is possible to modify the illustrated embodiments to include mixers or mixing elements on the walls of the channel of the fluid treatment system and/or the radiation source module, for example as taught in one or more of U.S. Pat. No. 5,846,437 [Whitby et al.], U.S. Pat. No. 6,015,229 [Cormack et al.], U.S. Pat. No. 6,126,841 [Whitby et al.], U.S. Pat. No. 6,224,759 [Whitby et al.] and U.S. Pat. No. 6,420,716 [Cormack et al.], and in International Publication Number WO 01/93995 [Brunet et al.]. Such mixers or mixing elements (sometimes also referred to in the art as "baffles") can be used to supplement or replace the use of so-called boundary lamps or boundary radiation source assemblies discussed above. Still further, it is possible to modify the illustrated embodiments to provide multiple banks of radiation source assemblies in hydraulic series. Still further, it is possible to modify the illustrated embodiments to utilized a radiation source assembly comprising a plurality of radiation sources disposed in a protective sleeve (i.e., sometimes referred to in the art as a "lamp bundle"). Still further, it is possible to modify the illustrated embodiments in FIGS. 1 and 2 such that banks 126 and 128 are disposed serially rather than in a side-by-side relationship (of course the dimensions of other elements of the fluid treatment system would need to be modified accordingly). It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A fluid treatment system comprising:
    an inlet;
    an outlet;
    a fluid treatment zone disposed between the inlet and the outlet, the fluid treatment zone having disposed therein an array of rows of radiation source assemblies;
    each radiation source assembly having a longitudinal axis transverse or parallel to a direction of fluid flow through the fluid treatment zone;
    each row comprising a plurality of radiation source assemblies in spaced relation in a direction transverse to the direction of fluid flow through the fluid treatment zone to define a gap through which fluid may flow between an adjacent pair of radiation source assemblies;
    all rows in the array being staggered with respect to one another in a direction orthogonal to the direction of fluid flow through the fluid treatment zone such that the gap between an adjacent pair of radiation source assemblies in an upstream row of radiation source assemblies is partially or completely obstructed in the direction of fluid flow by at least two serially disposed downstream rows of radiation source assemblies.

2. A fluid treatment system comprising:
an inlet;
an outlet;
a fluid treatment zone disposed between the inlet and the outlet, the fluid treatment zone having disposed therein an array of radiation source assemblies, each radiation source assembly having a longitudinal axis transverse to a direction of fluid flow through the fluid treatment zone;
the array of radiation source assemblies comprising: a first row of radiation source assemblies, a second row of radiation source assemblies downstream from the first row of radiation source assemblies, a third row of radiation source assemblies downstream from the second row of radiation source assemblies and a fourth row of radiation source assemblies downstream from the third row of radiation source assemblies;
an adjacent pair of radiation source assemblies in the first row defining a first gap through which fluid may flow, a radiation source assembly from the second row partially obstructing the first gap to divide the first gap into a second gap and a third gap, a radiation source assembly from the third row at least partially obstructing the second gap and a radiation source assembly from the fourth row at least partially obstructing the third gap.

3. The fluid treatment system defined in claim 2, wherein the fluid treatment system comprises a multiple number, N, of the array and N has a value of from 1 to 10.

4. The fluid treatment system defined in claim 2, wherein the fluid treatment zone comprises an open cross-section.

5. The fluid treatment system defined in claim 2, wherein the fluid treatment zone comprises an enclosure having a closed cross-section.

6. The fluid treatment system defined in claim 5, wherein the closed cross-section of the enclosure comprises a rectilinear shape.

7. The fluid treatment system defined in claim 2, wherein the fluid treatment zone has disposed therein: (i) an elongate first radiation source assembly having a first longitudinal axis, and (ii) an elongate second radiation source assembly having a second longitudinal axis; wherein the first longitudinal axis and the second longitudinal axis are non-parallel to each other and to a direction of fluid flow through the fluid treatment zone.

8. The fluid treatment system defined in claim 7, wherein the first radiation source assembly and the second radiation source assembly are oriented to define an acute angle between the first longitudinal axis and the second longitudinal axis.

9. The fluid treatment system defined in claim 7, wherein the first radiation source assembly and the second radiation source assembly are oriented to define an angle between the first longitudinal axis and the second longitudinal axis in the range of from about 15° about 170°.

10. The fluid treatment system defined in claim 7, wherein the first radiation source assembly and the second radiation source assembly are oriented to define an angle between the first longitudinal axis and the second longitudinal axis in the range of from about 35° about 120°.

11. The fluid treatment system defined claim 7, wherein the first radiation source assembly and the second radiation source assembly are oriented to define an angle between the first longitudinal axis and the second longitudinal axis in the range of from about 60° about 90°.

12. The fluid treatment system defined in claim 7, further comprising a support element for supporting a distal portion of the first radiation source assembly and a distal portion of the second radiation source assembly.

13. The fluid treatment system defined in claim 12, wherein the support element supports a portion of all radiation source assemblies present in the fluid treatment system.

14. The fluid treatment system defined in claim 12, wherein the support element comprises a post disposed substantially orthogonal to the direction of fluid flow through fluid treatment zone.

15. The fluid treatment system defined in claim 7, wherein the first radiation source assembly and the second radiation source assembly are co-planar.

16. The fluid treatment system defined in claim 7, wherein the first radiation source assembly and the second radiation source assembly are non-planar.

17. The fluid treatment system defined in claim 7, wherein the first radiation source assembly and the second radiation source assembly are oriented such that the first longitudinal axis and the second longitudinal axis converge toward the inlet.

18. The fluid treatment system defined in claim 7, wherein the first radiation source assembly and the second radiation source assembly are oriented such that the first longitudinal axis and the second longitudinal axis converge toward the inlet at a point downstream of the inlet.

19. The fluid treatment system defined in claim 7, wherein the first radiation source assembly and the second radiation source assembly are oriented such that the first longitudinal axis and the second longitudinal axis converge toward the outlet.

20. The fluid treatment system defined in claim 7, wherein the first radiation source assembly and the second radiation source assembly are oriented such that the first longitudinal axis and the second longitudinal axis converge toward the outlet at a point upstream of the outlet.

21. The fluid treatment system defined in claim 7, wherein the fluid treatment zone has disposed therein an array of radiation source assemblies arranged as: (i) a first bank of first radiation source assemblies, and (ii) a second bank of second radiation source assemblies.

22. The fluid treatment system defined in claim 2, wherein the fluid treatment zone has disposed therein an array of radiation source assemblies arranged as: (i) a first bank of first radiation source assemblies, and (ii) a second bank of second radiation source assemblies; wherein the first bank and the second bank are substantial mirror images of one another along a first plane disposed parallel to the direction of fluid flow through the fluid treatment zone.

23. The fluid treatment system defined in claim 2, wherein the fluid treatment zone has disposed therein an array of radiation source assemblies arranged as: (i) a first bank of first radiation source assemblies, and (ii) a second bank of second radiation source assemblies; wherein the first bank and the second bank are in a planar relationship in a second plane orthogonal to the first plane.

24. The fluid treatment system defined in claim 2, wherein the fluid treatment zone has disposed therein an array of radiation source assemblies arranged as: (i) a first bank of first radiation source assemblies, and (ii) a second bank of second radiation source assemblies; wherein the first bank and the second bank are in a non-planar relationship in a second plane orthogonal to the first plane.

25. The fluid treatment system defined in claim 2, further comprising a first transition zone interposed between the inlet and the fluid treatment zone, the first transition zone having a variable dimension orthogonal to the direction of fluid flow through the fluid treatment zone.

26. The fluid treatment system defined claim 2, further comprising: (i) a first transition zone interposed between the inlet and the fluid treatment zone, the first transition zone having a variable dimension orthogonal to the direction of fluid flow through the fluid treatment zone, and (ii) a second transition zone interposed between the fluid zone and the outlet, the second transition zone having a variable dimension orthogonal to the direction of fluid flow through the fluid treatment zone.

27. The fluid treatment system defined in claim 25, wherein the variable dimension increases in a direction toward the fluid treatment zone.

28. The fluid treatment system defined in claim 26, wherein each of the first transition zone and the second transition zone has a closed cross-section having an increasing cross-sectional area in a direction toward the fluid treatment zone.

29. The fluid treatment system defined in claim 26, wherein at least one of the first transition zone and the second transition zone comprises an intermediate transition region juxtaposed to the fluid treatment zone, the intermediate transition region having a variable dimension in first direction orthogonal to the direction of fluid flow through the fluid treatment zone and constant dimension in a second direction orthogonal to the first direction.

30. The fluid treatment system defined in claim 2, wherein the radiation source assembly comprises an ultraviolet radiation source.

31. The fluid treatment system defined in claim 2, wherein the fluid treatment zone comprises an enclosure having a pair of side walls interconnecting a top wall and a bottom wall.

32. The fluid treatment zone defined in claim 31, wherein a least portion of the top wall and the bottom wall each comprises a non-metallic material having greater radiation reflectance than metal.

33. A fluid treatment system comprising:
an inlet;
an outlet;
a fluid treatment zone disposed between the inlet and the outlet, the fluid treatment zone having disposed therein an array comprising 4 rows radiation source assemblies arranged serially from an upstream portion to a downstream portion of the fluid treatment zone;
each radiation source assembly having a longitudinal axis transverse to a direction of fluid flow through the fluid treatment zone;
wherein: (i) a first pair of rows of radiation source assemblies in the array comprise substantially uniform spacing between adjacent pairs of radiation source assemblies in the row; and (ii) a second pair of rows of radiation source assemblies in the array comprise substantially non-uniform spacing between adjacent pairs of radiation source assemblies in the row.

\* \* \* \* \*